US009051573B2

(12) United States Patent
Holland et al.

(10) Patent No.: US 9,051,573 B2
(45) Date of Patent: Jun. 9, 2015

(54) NEWLY DISCOVERED BACTERIUM IN THE FAMILY ACETOBACTERACEAE

(75) Inventors: Steven M. Holland, Bethesda, MD (US); David E. Greenberg, Bethesda, MD (US); Adrian Zelazny, Silver Spring, MD (US); Patrick Murray, Gibson Island, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1417 days.

(21) Appl. No.: 12/225,615

(22) PCT Filed: Mar. 28, 2007

(86) PCT No.: PCT/US2007/007795
§ 371 (c)(1),
(2), (4) Date: Sep. 16, 2009

(87) PCT Pub. No.: WO2007/126975
PCT Pub. Date: Nov. 8, 2007

(65) Prior Publication Data
US 2010/0055506 A1    Mar. 4, 2010

Related U.S. Application Data

(60) Provisional application No. 60/788,521, filed on Mar. 31, 2006.

(51) Int. Cl.
| | |
|---|---|
| *H01M 4/90* | (2006.01) |
| *H01M 8/16* | (2006.01) |
| *C12R 1/02* | (2006.01) |
| *C12N 15/52* | (2006.01) |
| *C12P 7/54* | (2006.01) |
| *C12R 1/01* | (2006.01) |

(52) U.S. Cl.
CPC . *C12N 15/52* (2013.01); *C12P 7/54* (2013.01); *C12R 1/01* (2013.01); *C12R 1/02* (2013.01); *H01M 4/90* (2013.01); *H01M 8/16* (2013.01); *Y02E 60/527* (2013.01)

(58) Field of Classification Search
None
See application file for complete search history.

(56) References Cited

U.S. PATENT DOCUMENTS

| | | | |
|---|---|---|---|
| 4,085,254 A | 4/1978 | Atkins | 429/2 |
| 4,578,323 A | 3/1986 | Hertl et al. | 429/15 |
| 4,581,336 A | 4/1986 | Malloy et al. | 435/176 |
| 4,683,195 A | 7/1987 | Mullis et al. | 435/6 |
| 4,683,202 A | 7/1987 | Mullis | 435/91 |
| 4,965,188 A | 10/1990 | Mullis et al. | 436/6 |
| 5,976,719 A | 11/1999 | Kim et al. | 429/2 |
| 6,190,903 B1 | 2/2001 | Weinstein et al. | 435/252.5 |
| 7,491,453 B2 | 2/2009 | Logan et al. | 429/2 |
| 2004/0048111 A1* | 3/2004 | Halme et al. | 429/2 |

OTHER PUBLICATIONS

Uhlig et al. International Journal of Systematic Bacteriology, Apr. 1986, p. 317-322.*
Chan et al. Biochem. J. (1991) 280, 139-146.*
Grundig et al. Arch Micrbiol (1987) 149:149-155.*
Stackebrandt, E. Food Technol. Biotechnol. 41 (1) 17-22 (2003).*
Anthony et al., "The Structure and Mechanism of Methanol Dehydrogenase,"*Biochim. Biophys. Acta.*, vol. 1647, pp. 18-23 (2001).
Asai et al., "The Flagellation and Taxonomy of Genera *Gluconobacter* and *Acetobacter* with Reference to the Existence of Intermediate Strains," *J. Gen. Appl. Microbiol.*, vol. 10, pp. 95-126 (1964).
Bartowsky et al., "Spoilage of Bottled Red Wine by Acetic Acid Bacteria," *Lett. Appl. Microbiol.*, vol. 36, pp. 307-314 (2003).
Bartual et al., "Development of a Multilocus Sequence Typing Scheme for Characterization of Clinical Isolates of *Acinetobacter baumannii*," *J. Clin. Microbiol.*, vol. 43, pp. 4382-4390 (2005).
Boesch et al., "*Acetobacter intermedius*, sp. nov.," *Syst. Appl. Microbiol.*, vol. 21, pp. 220-229 (1998).
Chongcharoen et al., "Adaptation and Acclimatization to Formaldehyde in Methylotrophs Capable of High-Concentration Formaldehyde Detoxification," *Microbiology*, vol. 151, pp. 2615-2622 (2005).
Cleenwerck et al., "Re-examination of the genus *Acetobacter*, with Descriptions of *Acetobacter cerevisiae* sp. nov. and *Acetobacter malorum* sp. nov.," *Int. J. Syst. Evol. Microbiol.*, vol. 52, pp. 1551-1558 (2002).
DelVecchio et al., "The Genome Sequence of the Facultative Intracellular Pathogen *Brucella melitensis*," *Proc. Natl. Acad. Sci. U.S.A.*, vol. 99, pp. 443-448 (2002).
Dorman et al., "*Nocardia* Infection in Chronic Granulomatous Disease," *Clin. Infect. Dis.*, vol. 35, pp. 390-394 (2002).
"Editorial: Cause and Effect," *Nat. Rev. Microbiol.*, vol. 4, pp. 414 (2006).
Eisen JA, "The RecA Protein as a Model Molecule for Molecular Systematic Studies of Bacteria: Comparison of Trees of RecAs and 16S rRNAs from the Same Species," *J. Mol. Evol.*, vol. 41, pp. 1105-1123 (1995).
Franke et al., "Description of *Gluconacetobacter sacchari* sp. nov., A New Species of Acetic Acid Bacterium Isolated from the Leaf Sheath of Sugar Cane and from the Pink Sugar-Cane Mealy Bug," *Int'l J. Syst. Bacteriol.*, vol. 49, pp. 1681-1693 (1999).
Fredricks et al., "The Acetobacteraceae: Extending the Spectrum of Human Pathogens," *PLoS Pathogens*, vol. 2, pp. 0249-0250 (2006).
Garcia-Martinez et al., "Use of the 16S-23S Ribosomal Genes Spacer Region in Studies of Prokaryotic Diversity," *J. Microbiol. Meth.*, vol. 36, pp. 55-64 (1999).

(Continued)

*Primary Examiner* — Oluwatosin Ogunbiyi
(74) *Attorney, Agent, or Firm* — Sheridan Ross P.C.

(57) ABSTRACT

Provided is an isolated novel Gram-negative bacterium, wherein the bacterium is an aerobic, facultative methylotroph that produces colonies that are yellow pigmented, wherein the bacterium can use methanol as a sole carbon source and can oxidize glucose and ethanol into acid. Also provided are novel purified polypeptides and isolated nucleic acids from the bacterium. Further provided are methods of using the bacterium and the purified polypeptides to degrade organic material and for use in biofuel cells.

76 Claims, 2 Drawing Sheets

(56) References Cited

OTHER PUBLICATIONS

Gevers et al., "Re-Evaluating Prokaryotic Species," *Nat. Rev. Microbiol.*, vol. 3, pp. 733-739 (2005).

Gonzalez et al., "Application of Molecular Methods for the Differentiation of Acetic Acid Bacteria in a Red Wine Fermentation," *J. Appl. Microbiol.*, vol. 96, pp. 853-860 (2004).

Greenberg et al., "A Novel Bacterium Associated with Lymphadenitis in a Patient with Chronic Granulomatous Disease," *PLoS Pathogens*, vol. 2, pp. 0260-0267 (2006).

Greenberg et al., "*Granulibacter bethesdensis* gen. nov., sp. nov., a Distinctive Pathogenic Acetic Acid Bacterium in the Family Acetobacteraceae," *Int. J. Syst. Evol. Microbiol.*, vol. 56, pp. 2609-2616 (2006).

Greenberg et al., "*Acetobacteraceae bacterium* CGDNIH1 16S Ribosomal RNA Gene, Partial Sequence," *A Novel Bacterium Associated with Lymphadenitis in a Patient with Chronic Granulomatous Disease*, XP-002451606 (2005).

Greenberg et al., "*Granulibacter bethesdensis* CGDNIH1, Complete Genome," *Genome Sequence Analysis of a Novel Human Pathogenic Acetic Acid Bacterium*, XP-002451609 (2006).

Guide et al., "Reinfection, Rather than Persistent Infection, in Patients with Chronic Granulomatous Disease," *J. Infect. Dis.*, vol. 187, pp. 845-853 (2003).

Gupta et al., "*Gluconobacter oxydans*: Its Biotechnological Applications," *J. Mol. Microbiol. Biotechnol.*, vol. 3, pp. 445-456 (2001).

Ivanova et al., "Genome Sequence of *Bacillus cereus* and Comparative Analysis with *Bacillus anthracis*," *Nature*, vol. 423, pp. 87-91 (2003).

Jackson et al., "The p47$^{phox}$ Mouse Knock-Out Model of Chronic Granulomatous Disease," *J. Exp. Med.*, vol. 182, pp. 751-758 (1995).

Jojima et al., "*Saccharibacter floricola* gen. nov., sp. nov., A Novel Osmophilic Acetic Acid Bacterium Isolated from Pollen," *Int. J. Syst. Evol. Microbiol.*, vol. 54, pp. 2263-2267 (2004).

Kapatral et al., "Genome Sequence and Analysis of the Oral Bacterium *Fusobacterium nucleatum* Strain ATCC 25586," *J. Bacteriol*, vol. 184, pp. 2005-2018 (2002).

Kaszycki et al., "Formaldehyde and Methanol Biodegradation with the Methylotrophic Yeast *Hansenula polymorpha* in a Model Wastewater System," *Microbiol. Res.*, vol. 154, pp. 289-296 (2000).

Katz et al., "Biochemical Fuel Cells," in *Handbook of Fuel Cells—Fundamentals, Technology and Applications*, Vielstich et al. (Eds.), Chap. 21, pp. 1-2, 9, 11-12 (2003).

Lekstrom-Himes et al., "Treatment with Intralesional Granulocyte Instillations and Interferon-γ for a Patient with Chronic Granulomatous Disease and Multiple Hepatic Abscesses," *Clin. Infect. Dis.*, vol. 19, pp. 770-773 (1994).

Liiv et al., "Multiple Functions of the Transcribed Spacers in Ribosomal RNA Operons," *Biol. Chem.*, vol. 379, pp. 783-793 (1998).

Lisdiyanti et al., "Identification of *Acetobacter* Strains Isolated from Indonesian Sources, and Proposals of *Acetobacter syzygii* sp. nov., *Acetobacter cibinongensis* sp. nov., and *Acetobacter orientalis* sp. nov.," *J. Gen. Appl. Microbiol.*, vol. 47, pp. 119-131 (2001).

Lisdiyanti et al., "Systematic Study of the Genus *Acetobacter* with Descriptions of *Acetobacter indonesiensis* sp. nov., *Acetobacter tropicalis* Sp. Nov., *Acetobacter orleanensis* (Hennberg 1906) comb. nov., *Acetobacter Lovaniensis* (Frateur 150) comb. nov., and *Acetobacter estunensis* (Carr 1958) comb. nov," *J. Gen. Appl. Microbiol.*, vol. 46, pp. 147-165 (2000).

Lisdiyanti et al., "*Kozakia baliensis* gen. nov., sp. nov., A Novel Acetic Acid Bacterium in the α-Proteobacteria," *Int. J. Syst. Evol. Microbiol.*, vol. 52, pp. 813-818 (2002).

Ludwig et al., "Bacterial Phylogeny Based on Comparative Sequence Analysis," *Electrophoresis*, vol. 19, pp. 554-568 (1998).

Macauley et al., "The Genus *Gluconobacter* and its Applications in Biotechnology," *Crit. Rev. Biotechnol.*, vol. 21, pp. 1-25 (2001).

McDonald et al., "The Methanol Dehydrogenase Structural Gene *mxaF* and its Use as a Functional Gene Probe for Methanotrophs and Methylotrophs," *Appl. Environ. Microbiol.*, vol. 63, pp. 3218-3224 (1997).

Nanda et al., "Characterization of Acetic Acid Bacteria in Traditional Acetic Acid Fermentation of Rice Vinegar (Komesu) and Unpolished Rice Vinegar (Kurosu) Produced in Japan," *Appl. Environ. Microbiol.*, vol. 67, pp. 986-990 (2001).

Nunn et al., "Methanol Dehydrogenase Subunit 1 Precursor (EC 1.1.99.8)," XP-002451608 (1990).

Page R, "TreeView: An Application to Display Phylogenetic Trees on Personal Computers," *Compt. Appl. Biosci.*, vol. 12, pp. 357-358 (1996).

Poblet et al., "Identification of Acetic Acid Bacteria by Restriction Fragment Length Polymorphism Analysis of a PCR-Amplified Fragment of the Gene Coding for 16S rRNA," *Lett. Appl. Microbiol.*, vol. 31, pp. 63-67 (2000).

Pollock et al., "Mouse Model of X-Linked Chronic Granulomatous Disease, an Inherited Defect in Phagocyte Superoxide Production," *Nat. Genet.*, vol. 9, pp. 202-209 (1995).

Ruiz et al., "Identification of Acetic Acid Bacteria by RFLP of PCR-Amplified 16S rDNA and 16S-23S rDNA Intergenic Spacer," *Int. J. Syst. Evol. Microbiol.*, vol. 50, pp. 1981-1987 (2000).

Seearunruangchai et al., "Identification of Acetic Acid Bacteria Isolated from Fruits Collected in Thailand," *J. Gen. Appl. Microbiol.*, vol. 50, pp. 47-53 (2004).

Segal et al., "Genetic, Biochemical, and Clinical Features of Chronic Granulomatous Disease," *Medicine*, vol. 79, pp. 170-200 (2000).

Sereti et al., "Disseminated Nocardiosis in a Patient with X-Linked Chronic Granulomatous Disease and Human Immunodeficiency Virus Infection," *Clin. Infect. Dis.*, vol. 33, pp. 235-239 (2001).

Shimwell et al., "Differentiation of *Acetomonas* and *Pseudomonas*," *J. Gen. Microbiol.*, vol. 23, pp. 283-286 (1960).

Shukla et al., "Biological Fuel Cells and Their Applications," *Curr. Sci.*, vol. 87, pp. 455-468 (2004).

Sievers et al., "Phylogenetic Identification of Two Major Nitrogen-Fixing Bacteria Associated with Sugarcane," *Syst. Appl. Microbiol.*, vol. 21, pp. 505-508 (1998).

Sievers et al., "Phylogenetic Position of *Gluconobacter* Species as a Coherent Cluster Separated from All *Acetobacter* Species on the Basis of 16S Ribosomal RNA Sequences," *FEMS Microbiol. Lett.*, vol. 126, pp. 123-126 (1995).

Snyder et al., "*Asaia bogorensis* Peritonitis Identified by 16S Ribosomal RNA Sequence Analysis in a Patient Receiving Peritoneal Dialysis," *Am. J. Kid. Dis.*, vol. 44, pp. e15-e17 (2004).

Sokollek et al., "Description of *Acetobacter oboediens* sp. nov. and *Acetobacter pomorum* sp. nov., Two New Species Isolated from Industrial Vinegar Fermentations," *Int. J. Syst. Bacteriol.*, vol. 48, pp. 935-940 (1998).

Speert et al., "Infection With *Pseudomonas cepacia* in Chronic Granulomatous Disease: Role of Nonoxidative Killing by Neutrophils in Host Defense," *J. Infect Dis.*, vol. 170, pp. 1524-1531 (1994).

Stackebrandt E, "The Richness of Prokaryotic Diversity: There Must Be a Species Somewhere," *Food Technol. Biotechnol.*, vol. 41, pp. 17-22 (2003).

Tanasupawat et al., "*Gluconobacter thailandicus* sp. nov., An Acetic Acid Bacterium in the α-Proteobacteria," *J. Gen. Appl. Microbiol.*, vol. 50, pp. 159-167 (2004).

Thompson et al., "Phylogeny and Molecular Identification of Vibrios on the Basis of Multilocus Sequence Analysis," *Appl. Environ. Microbiol.*, vol. 71, pp. 5107-5115 (2005).

Winkelstein et al., "Chronic Granulomatous Disease: Report on a National Registry of 368 Patients," *Medicine*, vol. 79, pp. 155-169 (2000).

Yamada et al., "Identification of Acetic Acid Bacteria Isolated from Indonesian Sources, Especially of Isolates Classified in the Genus *Gluconobacter*," *J. Gen. Appl. Microbiol.*, vol. 45, pp. 23-28 (1999).

Yamada et al., "*Asaia bogorensis* gen. nov., sp. nov., An Unusual Acetic Acid Bacterium in the α-Proteobacteria," *Int. J. Syst. Evol. Microbiol.*, vol. 50, pp. 823-829 (2000).

Yamashita et al., "Emendation of the Genus *Acidimonas* Urakami, Tamaoka, Suzuki and Komagata 1989," *Int. J. Syst. Evol. Microbiol.*, vol. 54, pp. 865-870 (2004).

(56) References Cited

OTHER PUBLICATIONS

Yukphan et al., "Identification of Strains Assigned to the Genus *Gluconobacter* Asai 1935 Based on the Sequence and the Restriction Analyses of the 16S-23S rDNA Internal Transcribed Spacer Regions," *J. Gen. Appl. Microbiol.*, vol. 50, pp. 9-15 (2004).

Yukphan et al., "Re-identification of *Gluconobacter* Strains based on Restriction Analysis of 16S-23S rDNA Internal Transcribed Spacer Regions," *J. Gen. Appl. Microbiol.*, vol. 50, pp. 189-195 (2004).

Zeigler DR, "Gene Sequences Useful for Predicting Relatedness of Whole Genomes in Bacteria," *Int. J. Syst. Evol. Microbiol.*, vol. 53, pp. 1893-1900 (2003).

* cited by examiner

NEWLY DISCOVERED BACTERIUM IN THE FAMILY ACETOBACTERACEAE

CROSS REFERENCE TO RELATED APPLICATIONS

This application claims priority to U.S. provisional application No. 60/788,521, filed on Mar. 31, 2006. The aforementioned application is herein incorporated by this reference in its entirety.

This invention was made with government support awarded by the National Institutes of Health. The United States government has certain rights in the invention.

SEQUENCE LISTING STATEMENT

This application is filed with four (4) identical CD-ROM disks: Copy 1, Copy 2, Copy 3 and Copy 4 in computer readable form, all of which contain the sequence listing of the claimed amino acid and nucleic acid sequences which are hereby incorporated by this reference in their entirety.

BACKGROUND OF THE INVENTION

1. Field of the Invention

This invention relates generally to the discovery of a novel bacterium found in lymph nodes of a subject diagnosed with chronic granulomatous disease. Specifically, the invention relates to a new genus and species of bacteria, designated *Granulibacter bethesdensis*, and uses thereof.

2. Background Art

Human industrial activities inevitably generate industrial wastes. These industrial wastes comprise organic materials, for example methanol, formaldehyde, and ethanol. The high costs of degrading these wastes are borne by industry. These costs hinder market expansion for these and other related businesses.

It would be useful to manufacture and market a biomass degrading and treatment method capable of converting organic waste materials into non-toxic end-products. Such a method would include a system for treating organic waste and a new degrading agent, for example a novel bacterium. Using such a system, a person can 1) reduce waste treatment costs, 2) prevent pollution of the environment, and 3) improve soil, e.g. farmlands.

Further, it would be useful to mass produce and purify the plurality of polypeptide enzymes that the bacterium uses to degrade organic material and use the enzymes to degrade organic material in situations where the presence of the bacterium may not be necessary. Moreover, the purified polypeptide enzymes can be used in small biofuel cells to produce electrical energy from the degradation of organic materials.

Accordingly, applicants isolated a novel bacterium from a subject diagnosed with chronic granulomatous disease and discovered that the bacterium is capable of degrading methanol, formaldehyde, ethanol, and their respective intermediate breakdown products into non-toxic end-products. Examples of non-toxic end-products include, but are not limited to carbon dioxide, hydrogen ions, and acetic acid. Such a bacterium can be useful for many different purposes in biodegradation of organic waste and in the production of electrical energy.

Chronic granulomatous disease (CGD) is a rare inherited disease of the phagocyte NADPH oxidase system that leads to defective production of toxic oxygen metabolites and impaired killing of certain microbes [1]. Clinically, patients develop recurrent life-threatening infections with catalase-producing organisms as well as tissue granuloma formation [2]. The bacteria and fungi that commonly cause infection in CGD include *Staphylococcus aureus, Serratia marcescens, Burkholderia cepacia, Nocardia* and *Aspergillus* species [3-7]. Rare infections with organisms only encountered in CGD, such as *Paecilomyces* sp. and *Trichosporon inkin*, suggest that CGD patients have a unique susceptibility pattern [1]. However, when a specific microbiologic diagnosis cannot be made, patients are frequently treated with broad-spectrum antimicrobials that cover the most likely pathogens.

In the course of evaluation of fever and lymphadenitis in a CGD patient, a novel Gram-negative bacterium was identified that belongs to the family Acetobacteraceae, bacteria that are found widely in the environment. These bacteria have a variety of industrial uses, for example the production of vinegar. What is needed in the art is a bacterium that can use methanol as its sole carbon source and that can degrade organic material, e.g., methanol, formaldehyde, and ethanol, into non-toxic end-products. Such a bacterium can also be used in a biofuel cell to convert organic material into carbon dioxide and electrical energy.

SUMMARY OF THE INVENTION

In accordance with the purposes of this invention, as embodied and broadly described herein, this invention, in one aspect, relates to an isolated Gram-negative bacterium, wherein the bacterium is an aerobic, facultative methylotroph that produces colonies that are yellow pigmented, wherein the bacterium can use methanol as a sole carbon source and can oxidize glucose and ethanol into acid.

In another aspect, the invention relates to a method of degrading an organic material, comprising contacting the organic material with an effective, degrading amount of an isolated Gram-negative bacterium, wherein the bacterium is an aerobic, facultative methylotroph that produces colonies that are yellow pigmented, wherein the bacterium can use methanol as a sole carbon source and can oxidize glucose and ethanol into acid, whereby contacting the organic material with the bacterium degrades the organic material.

In another aspect, the invention relates to a method for growing an isolated Gram-negative bacterium, designated *Granulibacter bethesdensis* and deposited under ATCC Accession No. BAA-1260 in accordance with the terms of the Budapest Treaty with the American Type Culture Collection (ATCC), Manassas, VA, on Nov. 18,2005 and DSM Accession No. 17861, wherein the bacterium is an aerobic, facultative methylotroph that produces colonies that are yellow pigmented, wherein the bacterium can use methanol as a sole carbon source and can oxidize glucose and ethanol into acid, comprising culturing the bacterium at a temperature and on a medium effective to promote growth of the bacterium.

In another aspect, the invention relates to a biofuel cell, comprising a cathode, an anode, a conductive medium, an ion exchange membrane interposed between the cathode and the anode, and a bacterial catalyst around the anode, wherein the bacterial catalyst comprises an isolated Gram-negative bacterium, wherein the bacterium is an aerobic, facultative methylotroph that produces colonies that are yellow pigmented, wherein the bacterium can use methanol as a sole carbon source and can oxidize glucose and ethanol into acid.

In another aspect, the invention relates to a plurality of purified polypeptides that can degrade organic material and can convert chemical energy in organic material into electrical energy.

In another aspect, the invention relates to a plurality of isolated antibodies that specifically bind to the disclosed purified polypeptides.

In yet another aspect, the invention relates to isolated nucleic acids that encode the purified polypeptides that can degrade organic material and can convert chemical energy in organic material into electrical energy.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawing, which is incorporated in and constitutes a part of this specification, illustrates one embodiment of the invention and together with the description, serves to explain the principles of the invention.

DESCRIPTION OF THE PREFERRED EMBODIMENTS

Figure 1:
FIG. 1 shows a phylogram of the 16S rRNA gene sequences of members of the Acetobacteraceae. The 16S rRNA gene sequence of *Stella humosa* was used as an outgroup. The tree was constructed with Clustal W and the neighbour-joining method with 1000 bootstrap replicates. Numbers at nodes are percentage of bootstrap replicates that supported this pattern (only values of 50% or higher shown). The scale bar for the branch lengths represents the number of substitutions per site. Abbreviations: T, type strain.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific purified proteins, or to particular nucleic acids, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a purified polypeptide" includes mixtures of two or more purified polypeptides.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings.

"Optional" or "optionally" means that the subsequently described event or circumstance may or may not occur, and that the description includes instances where said event or circumstance occurs and instances where it does not. For example, the phrase "the medium can optionally contain glucose" means that the medium may or may not contain glucose as an ingredient and that the description includes both media containing glucose and media not containing glucose.

Provided herein is an isolated Gram-negative bacterium, wherein the bacterium is an aerobic, facultative methylotroph that produces colonies that are yellow pigmented, wherein the bacterium can use methanol as a sole carbon source and can oxidize glucose and ethanol into acid. An example of the bacterium is designated *Granulibacter bethesdensis*, having the ATCC patent deposit designation BAA-1260. As used herein, "facultative" means not required or compulsory. As used herein, a "methylotroph" is a bacterium that can use methanol as a source of energy. Thus, for example, a facultative methylotroph is a bacterium that can grow either in the presence or in the absence of methanol. Therefore, the Gram-negative bacterium of the present invention can grow in the presence of methanol, but the bacterium does not require methanol to grow. These Gram-negative rods were isolated from three cervical lymph nodes from a subject diagnosed with chronic granulomatous disease (CGD) and were cultured on BCYE plates (Remel) after four days' incubation at 35° C. As used herein, by "subject" is meant an individual. Preferably, the subject is a mammal such as a primate, and, more preferably, a human. The term "subject" includes domesticated animals, such as cats, dogs, etc., livestock (e.g., cattle, horses, pigs, sheep, goats, etc.), and laboratory animals (e.g., mouse, rabbit, rat, gerbil, guinea pig, etc.).

The organism is a non-motile coccobacillus that is catalase-positive and oxidase-negative. Tests for the presence of lysine and ornithine decarboxylases and arginine dihydrolase were negative. The bacterium is urease-positive and weakly ferments glucose; it does not produce acid from lactose, mannitol, sucrose, maltose or xylose. These results were confirmed at the Centers for Disease Control and Prevention (CDC).

The API 20 NE (BioMerieux) and RapID NH (Remel) commercial kits generated codes 0200000 and 1501, respectively, neither of which yielded an identification. In view of the failure of conventional tests to identify the organism and its fastidious growth characteristics, the 16S rRNA gene was sequenced, and a search for related sequences was made in GenBank. The best 50 matches by BLAST search were all members of the family Acetobacteraceae, with the closest match being *Gluconacetobacter sacchari* (95.7% similarity; accession no. AF127412) and *Gluconacetobacter liquefaciens* (95.5% similarity; accession no. X75617). The 16S rDNA sequence similarity between the subject's isolate and other commonly encountered pathogenic Gram-negative rods was very low (~80%). A phylogenetic tree of *Granulibacter bethesdensis* based on its 16S RNA sequence is shown in FIG. 1.

The family Acetobacteraceae comprises several genera including the genus *Gluconacetobacter* and *Acetobacter*. The closest 16S rRNA gene sequence match was to *Gluconacetobacter sacchari* at 95.7%. However, strains that have a 16S rDNA sequence similarity below 97% are not considered the same species [9]. A polyphasic taxonomic approach shows that this organism belongs to a new genus and species in this family. Members of the genera *Gluconacetobacter, Acetobacter, Gluconobacter* and *Acidomonas* [10] have been called the acetic acid bacteria because they derive energy from the aerobic oxidation of ethanol to acetic acid. They have been cultured from fruits, fermented foods, plants, soil and water [11-14], are utilized industrially in the production of vinegar, and are encountered during the fermentation of wine. Characteristics that differentiate the new genus *Granulibacter* from other genera of acetic acid bacteria are shown below in Table 1.

Bacteria decompose or biodegrade organic molecules as part of their need to derive chemical energy to make ATP or produce metabolic intermediates. Being a methylotrophic organism, *G. bethesdensis* contains the biochemical pathways needed to degrade methanol into carbon dioxide.

For methanol to be biodegraded, it must first be converted into formaldehyde. Formaldehyde is a potent poison that must be broken down quickly in methylotrophic organisms such as *G. bethesdensis*, or else the bacterium will die. Just as this organism can degrade formaldehyde to detoxify its own internal environment, it can be used to degrade formaldehyde in the external environment. Moreover, the bacterium's purified polypeptide enzymes, for example methanol dehydrogenase and formaldehyde-activating enzyme, can be produced in large quantities by methods known to persons skilled in the art and can be used in the removal of industrial pollutants, for example, methanol and formaldehyde.

Further, *Granulibacter bethesdensis* belongs to a family of bacteria collectively referred to as the acetic acid bacteria. Thus, the bacterium can convert alcohols, for example ethanol, into acetic acid (vinegar) which has many industrial uses.

In one aspect, the bacterium comprises a genome identified as SEQ ID NO:1 which is deposited under GenBank Accession No. CP000394. In another aspect, the bacterium comprises a 16SRNA nucleic acid that is greater than about 98% similar to the nucleic acid identified as SEQ ID NO:2. In another aspect, the bacterium comprises a 16SRNA nucleic acid that is greater than about 99% similar to the nucleic acid identified as SEQ ID NO:2. In yet another aspect, the bacterium comprises a 16SRNA nucleic acid identified as SEQ ID NO:2.

Further, the bacterium is a facultative methylotroph that can degrade organic material into carbon dioxide and water. For example, the bacterium can degrade methanol into carbon dioxide and hydrogen ions. In another aspect, the bacterium can degrade ethanol into acetic acid. In order to use methanol, for example, as a carbon source for energy, the bacterium comprises a plurality of novel polypeptides that are enzymes that in vivo metabolize methanol. Each disclosed purified polypeptide, designated by its respective sequence identification number, is listed in Table 3, adjacent to the polypeptide known in the art that is most similar to it.

Figure 2:
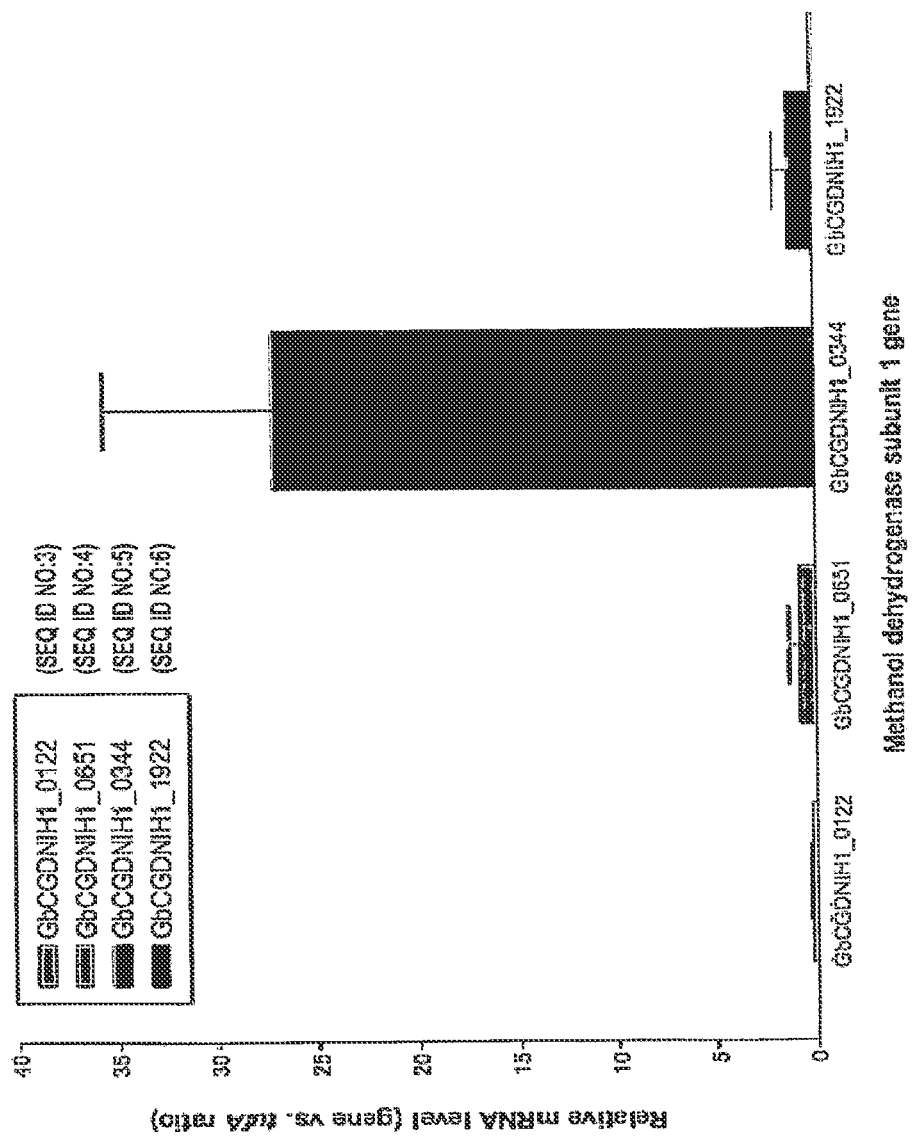
FIG. 2 shows quantitative RNA analysis of methanol dehydrogenase and selected virulence gene expression. Cumulative data from 5 different Taqman experiments analyzing gene expression in vitro at 26° C. late log phase, 26° C. stationary phase, 37° C. mid log phase, 37° C. late log phase and 37° C. stationary phase growth of the methanol dehydrogenase genes shown. GbCGDNIH1_0122 is SEQ ID NO:3; GbCGDNIH1_0651 is SEQ ID NO:4; GbCGDNIH1_0344 is SEQ ID NO:5; and GbCGDNIH1_1922 is SEQ ID NO:6.

In one aspect, the bacterium produces methanol dehydrogenase, wherein the methanol dehydrogenase oxidizes methanol into formaldehyde. The methanol dehydrogenase comprises two subunits, a first subunit and a second subunit. The first subunit comprises one polypeptide that can be any one of four polypeptides. RT-PCR of GbCGDNIH1_0122 (SEQ ID NO:3), GbCGDNIH1_0651 (SEQ ID NO:4), GbCGDNIH1_0344 (SEQ ID NO:5), and GbCGDNIH1_1922 (SEQ ID NO:6) from in vitro cultivated organisms from early, mid, late log and stationary phase growth at 25° C. and 37° C., respectively, showed that GbCGDNIH1_0344 (SEQ ID NO:5) is highly expressed relative to the three other ORFs (FIG. 2). Thus, the first subunit can be one polypeptide selected from the group consisting of a first polypeptide having an amino acid sequence identified as SEQ ID NO:3, a second polypeptide having an amino acid sequence identified as SEQ ID NO:4, a third polypeptide having an amino acid sequence identified as SEQ ID NO:5, and a fourth polypeptide having an amino acid sequence identified as SEQ ID NO:6.

Therefore, in one aspect, the first subunit methanol dehydrogenase polypeptide has an amino acid sequence greater than about 61% similar to an amino acid sequence identified as SEQ ID NO:3. Thus, the first subunit polypeptide can be greater than about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:3. Therefore, in one aspect, the first subunit polypeptide has an amino acid sequence identified as SEQ ID NO:3.

Alternatively, the first subunit polypeptide has an amino acid sequence greater than about 70% similar to an amino acid sequence identified as SEQ ID NO:4. Thus, the first subunit polypeptide can be greater than about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:4. Therefore, in one aspect, the first subunit polypeptide has an amino acid sequence identified as SEQ ID NO:4.

Alternatively, the first subunit polypeptide has an amino acid sequence greater than about 77% similar to an amino acid sequence identified as SEQ ID NO:5. Thus, the first subunit polypeptide can be greater than about 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:5. Therefore) in one aspect, the first subunit polypeptide has an amino acid sequence identified as SEQ ID NO:5.

Alternatively, the first subunit polypeptide has an amino acid sequence greater than about 72% similar to an amino acid sequence identified as SEQ ID NO:6. Thus, the first subunit polypeptide can be greater than about 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:6. Therefore, in one aspect, the first subunit polypeptide has an amino acid sequence identified as SEQ ID NO:6.

The second subunit polypeptide has an amino acid sequence greater than about 64% similar to an amino acid sequence identified as SEQ ID NO:7. Thus, the second subunit polypeptide can be greater than about 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:7. Therefore, in one aspect, the second subunit polypeptide has an amino acid sequence identified as SEQ ID NO:7.

In another aspect, the disclosed bacterium produces a methanol dehydrogenase first subunit polypeptide having an amino acid sequence identified as SEQ ID NO:3, which is encoded by a nucleic acid having a nucleic acid sequence identified as SEQ ID NO:8.

In another aspect, the disclosed bacterium produces a methanol dehydrogenase first subunit polypeptide having an amino acid sequence identified as SEQ ID NO:4, which is encoded by a nucleic acid having a nucleic acid sequence identified as SEQ ID NO:9.

In another aspect, the disclosed bacterium produces a methanol dehydrogenase first subunit polypeptide having an amino acid sequence identified as SEQ ID NO:5, which is encoded by a nucleic acid having a nucleic acid sequence identified as SEQ ID NO:10.

In another aspect, the disclosed bacterium produces a methanol dehydrogenase first subunit polypeptide having an amino acid sequence identified as SEQ ID NO:6, which is encoded by a nucleic acid having a nucleic acid sequence identified as SEQ ID NO:11.

In another aspect, the disclosed bacterium produces a methanol dehydrogenase second subunit polypeptide having an amino acid sequence identified as SEQ ID NO:7, which is encoded by a nucleic acid having a nucleic acid sequence identified as SEQ ID NO:12.

In another aspect, the bacterium disclosed herein produces formaldehyde-activating enzyme that has an amino acid sequence greater than about 82% similar to an amino acid sequence identified as SEQ ID NO:13, wherein the formaldehyde-activating enzyme converts formaldehyde into methylene tetrahydromethanopterin. Thus, the formaldehyde-activating enzyme can be greater than about 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:13. Therefore, in one aspect, the formaldehyde-activating enzyme has an amino acid sequence identified as SEQ ID NO:13, which is encoded by a nucleic acid having a nucleic acid sequence identified as SEQ ID NO:14.

In another aspect, the bacterium produces methylenetetrahydromethanopterin dehydrogenase (NAD+/NADP) that has an amino acid sequence greater than about 54% similar to an amino acid sequence identified as SEQ ID NO:15, wherein the methylenetetrahydromethanopterin dehydrogenase (NAD+/NADP) converts methylene tetrahydromethanopterin into methenyl tetrahydromethanopterin. Thus, the methylenetetrahydromethanopterin dehydrogenase (NAD+/NADP) can be greater than about 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:15. Therefore, in one aspect, the methylenetetrahydromethanopterin dehydrogenase (NAD+/NADP) has an amino acid sequence identified as SEQ ID NO:15, which is encoded by a nucleic acid having a nucleic acid sequence identified as SEQ ID NO:16.

In another aspect, the bacterium produces N5N10-methenyltetrahydromethanopterin cyclohydrolase that has an amino acid sequence greater than about 62% similar to an amino acid sequence identified as SEQ ID NO:17, wherein the N5N10-methenyltetrahydromethanopterin cyclohydrolase converts methenyl tetrahydromethanopterin into 5-formyl tetrahydromethanopterin. Thus, the N5N10-methenyltetrahydromethanopterin cyclohydrolase can be greater than about 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:17. Therefore, in one aspect, the N5N10-methenyltetrahydromethanopterin cyclohydrolase has an amino acid sequence identified as SEQ ID NO:17, which is encoded by a nucleic acid having a nucleic acid sequence identified as SEQ ID NO:18.

In another aspect, the bacterium produces formylmethanofuran-tetrahydromethanopterin formyltransferase that has an amino acid sequence greater than about 62% similar to an amino acid sequence identified as SEQ ID NO:19, wherein the formylmethanofuran-tetrahydromethanopterin formyltransferase converts 5-formyl tetrahydromethanopterin into formyl methanofuran. Thus, the formylmethanofuran-tetrahydromethanopterin formyltransferase can be greater than about 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:19. Therefore, in one aspect, the formylmethanofuran-tetrahydromethanopterin formyltransferase has an amino acid sequence identified as SEQ ID NO:19, which is encoded by a nucleic acid having a nucleic acid sequence identified as SEQ ID NO:20.

In another aspect, the bacterium produces tungsten-containing formylmethanofuran dehydrogenase that converts formyl methanofuran into formate. Tungsten-containing formylmethanofuran dehydrogenase comprises a subunit (c) polypeptide, a subunit (a) polypeptide, and a subunit (b) polypeptide.

In one aspect, the subunit (c) polypeptide has an amino acid sequence greater than about 46% similar to an amino acid sequence identified as SEQ ID NO:21. Thus, the subunit (c) polypeptide can be greater than about 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:21. Therefore, in one aspect, the subunit (c) polypeptide has an amino acid sequence identified as SEQ ID NO:21, which is encoded by a nucleic acid having a nucleic acid sequence identified as SEQ ID NO:24.

In another aspect, the subunit (a) polypeptide has an amino acid sequence greater than about 52% similar to an amino acid sequence identified as SEQ ID NO:22. Thus, the subunit (a) polypeptide can be greater than about 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:22. Therefore, in one aspect, the subunit (a) polypeptide has an amino acid sequence identified as SEQ ID NO:22, which is encoded by a nucleic acid having a nucleic acid sequence identified as SEQ ID NO:25.

In yet another aspect, the subunit (b) polypeptide has an amino acid sequence greater than about 32% similar to an amino acid sequence identified as SEQ ID NO:23. Thus, the subunit (b) polypeptide can be greater than about 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:23. Therefore, in one aspect, the subunit (b) polypeptide has an amino acid sequence identified as SEQ ID NO:23, which is encoded by a nucleic acid having a nucleic acid sequence identified as SEQ ID NO:26.

In another aspect, the bacterium produces methylenetetrahydrofolate dehydrogenase (NADP+) that has an amino acid sequence greater than about 62% similar to an amino acid sequence identified as SEQ ID NO:27, wherein the methylenetetrahydrofolate dehydrogenase (NADP+) converts N5N10-methylene tetrahydrofolate into N5N10-methenyl tetrahydrofolate. Thus, the methylenetetrahydrofolate dehydrogenase (NADP+) can be greater than about 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:27. Therefore, in one aspect, the methylenetetrahydrofolate dehydrogenase (NADP+) has an amino acid sequence identified as SEQ ID NO:27, which is encoded by a nucleic acid having a nucleic acid sequence identified as SEQ ID NO:28.

In yet another aspect, the bacterium produces methylenetetrahydrofolate cyclohydrolase that has an amino acid sequence greater than about 64% similar to an amino acid sequence identified as SEQ ID NO:29, wherein the methylenetetrahydrofolate cyclohydrolase converts N5N10-methenyl tetrahydrofolate into N10-formyl tetrahydrofolate. Thus, the methylenetetrahydrofolate cyclohydrolase can be greater than about 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:29. Therefore, in one aspect, the methylenetetrahydrofolate cyclohydrolase has an amino acid sequence identified as SEQ ID NO:29, which is encoded by a nucleic acid identified as SEQ ID NO:30.

In another aspect, the bacterium produces formate-tetrahydrofolate ligase that has an amino acid sequence greater than about 69% similar to an amino acid sequence identified as SEQ ID NO:31, wherein the formate-tetrahydrofolate ligase converts N10-formyl tetrahydrofolate into formate. Thus, the formate-tetrahydrofolate ligase can be greater than about 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:31. Therefore, in one aspect, the formate-tetrahydrofolate ligase has an amino acid sequence identified as SEQ ID NO:31, which is encoded by a nucleic acid identified as SEQ ID NO:32.

In another aspect, the bacterium produces formate dehydrogenase, wherein the formate dehydrogenase converts formate into carbon dioxide. The formate dehydrogenase comprises a first subunit polypeptide, a second subunit polypeptide, a third subunit polypeptide, a fourth subunit polypeptide, and a fifth subunit polypeptide. Thus, provided is a first subunit polypeptide having an amino acid sequence greater than about 62% similar to an amino acid sequence identified as SEQ ID NO:33. Thus, the first subunit polypeptide can be greater than about 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:33. Therefore, in one aspect, the first subunit polypeptide has an amino acid sequence identified as SEQ ID NO:33, which is encoded by a nucleic acid identified as SEQ ID NO:38.

Further provided is a second subunit polypeptide having an amino acid sequence greater than about 74% similar to an amino acid sequence identified as SEQ ID NO:34. Thus, the second subunit polypeptide can be greater than about 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:34. Therefore, in one aspect, the second subunit polypeptide has an amino acid sequence identified as SEQ ID NO:34, which is encoded by a nucleic acid identified as SEQ ID NO:39.

Further provided is a third subunit polypeptide having an amino acid sequence greater than about 77% similar to an amino acid sequence identified as SEQ ID NO:35. Thus, the third subunit polypeptide can be greater than about 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:35. Therefore, in one aspect, the third subunit polypeptide has an amino acid sequence identified as SEQ ID NO:35, which is encoded by a nucleic acid identified as SEQ ID NO:40.

Further provided is a fourth subunit polypeptide having an amino acid sequence greater than about 46% similar to an amino acid sequence identified as SEQ ID NO:36. Thus, the fourth subunit polypeptide can be greater than about 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:36. Therefore, in one aspect, the fourth subunit polypeptide has an amino acid sequence identified as SEQ ID NO:36, which is encoded by a nucleic acid identified as SEQ ID NO:41.

Also provided is a fifth subunit polypeptide having an amino acid sequence greater than about 62% similar to an amino acid sequence identified as SEQ ID NO:37. Thus, the fifth subunit polypeptide can be greater than about 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:37. Therefore, in one aspect, the fifth subunit polypeptide has an amino acid sequence identified as SEQ ID NO:37, which is encoded by a nucleic acid identified as SEQ ID NO:42.

In another aspect, the bacterium produces an aldehyde dehydrogenase, wherein the aldehyde dehydrogenase oxidizes acetaldeyde into acetic acid. The aldehyde dehydrogenase comprises a first subunit polypeptide, a second subunit polypeptide, and a third subunit polypeptide. Thus, provided is a first subunit polypeptide having an amino acid sequence greater than about 51% similar to an amino acid sequence identified as SEQ ID NO:43. Thus, the first subunit polypeptide can be greater than about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:43. Therefore, in one aspect, the first subunit polypeptide has an amino acid sequence identified as SEQ ID NO:43, which is encoded by a nucleic acid identified as SEQ ID NO:46.

Also provided is a second subunit polypeptide having an amino acid sequence greater than about 54% similar to an amino acid sequence identified as SEQ ID NO:44. Thus, the second subunit polypeptide can be greater than about 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%; 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:44. Therefore, in one aspect, the second subunit polypeptide has an amino acid sequence identified as SEQ ID NO:44, which is encoded by a nucleic acid identified as SEQ ID NO:47.

Further provided is a third subunit polypeptide having an amino acid sequence greater than about 73% similar to an amino acid sequence identified as SEQ ID NO:45. Thus, the third subunit polypeptide can be greater than about 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:45. Therefore, in one aspect, the third subunit polypeptide has an amino acid sequence identified as SEQ ID NO:45.

In another aspect; the bacterium produces an alcohol dehydrogenase, wherein the alcohol dehydrogenase oxidizes methanol into formaldehyde or ethanol into acetaldehyde. In one aspect, the alcohol dehydrogenase has an amino acid sequence greater than about 59% similar to an amino acid sequence identified as SEQ ID NO:48. Thus, the alcohol dehydrogenase can be greater than about 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similar to an amino acid sequence identified as SEQ ID NO:48. Therefore, in one aspect, the alcohol dehydrogenase has an amino acid sequence identified as SEQ ID NO:48, which is encoded by a nucleic acid identified as SEQ ID NO:49.

Further provided is a purified polypeptide selected from the group of purified polypeptides having amino acid sequences identified as SEQ ID NO:3, SEQ ID NO:4, SEQ ID NO:5, SEQ ID NO:6, SEQ ID NO:7, SEQ ID NO:13, SEQ ID NO:15, SEQ ID NO:17, SEQ ID NO:19, SEQ ID NO:21, SEQ ID NO:22, SEQ ID NO:23, SEQ ID NO:27, SEQ ID NO:29, SEQ ID NO:31, SEQ ID NO:33, SEQ ID NO:34, SEQ ID NO:35, SEQ ID NO:36, SEQ ID NO:37, SEQ ID NO:43, SEQ ID NO:44, SEQ ID NO:45, SEQ ID NO:48, wherein each polypeptide, alone or in combination with one or more disclosed polypeptides, can degrade an organic material, for example methanol, formaldehyde, ethanol, and intermediate breakdown products thereof. Examples of the end-products that result from the degradation of the organic materials include carbon dioxide, hydrogen ions and acetic acid. The energy produced from the biodegradation process can be heat energy, chemical energy, or electrical energy.

As used herein, a "purified polypeptide" or "isolated polypeptide" is a polypeptide that is substantially free from the materials with which the polypeptide is normally associated in nature or in culture. The polypeptides of the invention can be obtained, for example, by extraction from a natural source, for example, an isolated Gram-negative bacterium, wherein the bacterium is an aerobic, facultative methylotroph that produces colonies that are yellow pigmented, wherein the bacterium can use methanol as a sole carbon source and can oxidize glucose and ethanol into acid; by expression of a recombinant nucleic acid encoding the polypeptide (for example, in a cell or in a cell-free translation system); or by chemically synthesizing the polypeptide. In addition, a polypeptide may be obtained by cleaving full-length polypeptides. When the polypeptide is a fragment of a larger naturally occurring polypeptide, the purified (isolated) polypeptide is shorter than and excludes the full-length, naturally-occurring polypeptide of which it is a fragment.

The disclosed novel polypeptides can be prepared by using any of a number of chemical polypeptide synthesis techniques well-known to those of ordinary skill in the art, including solution methods and solid phase methods. One method of producing the disclosed polypeptides is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to an antigen of the present invention, for example, can be synthesized by standard chemical reactions.

For example, enzymatic ligation of cloned or synthetic peptide segments allows relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intra-molecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K. et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp 257-267 (1992)).

The polypeptides of the invention can also be prepared by other means including, for example, recombinant techniques. Examples of appropriate cloning and sequencing techniques, and instructions sufficient to direct persons of skill through many cloning exercises are found in Sambrook et al. (2001) Molecular Cloning—A Laboratory Manual (3rd ed.) Vol. 1-3, Cold Spring Harbor Laboratory, Cold Spring Harbor Press, NY, (Sambrook).

It is understood that as discussed herein, the terms "similar" or "similarity" mean the same thing as "homology" and "identity." Thus, for example, if the use of the word homology is used to refer to two non-natural sequences, it is understood that this is not necessarily indicating an evolutionary relationship between these two sequences, but rather is looking at the similarity or relatedness between their nucleic acid or amino acid sequences. Many of the methods for determining similarity between two evolutionarily related molecules are routinely applied to any two or more nucleic acids or polypeptides for the purpose of measuring sequence similarity regardless of whether they are evolutionarily related.

In general, it is understood that one way to define any known variants and derivatives or those that might arise, of the disclosed nucleic acids and polypeptides herein, is through defining the variants and derivatives in terms of similarity, or homology, to specific known sequences. In general, variants of nucleic acids and polypeptides herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent similarity, or homology, to the stated sequence or the native sequence. Those of skill in the art readily understand how to determine the similarity of two polypeptides or nucleic acids. For example, the similarity can be calculated after aligning the two sequences so that the similarity is at its highest level.

Another way of calculating similarity, or homology, can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444(1988), by computerized implementations of these algorithms (GAP, BESTFIT, FASTA, and TFASTA in the Wisconsin Genetics Software Package, Genetics Computer Group, 575 Science Dr., Madison, WI; the BLAST algorithm of Tatusova and Madden FEMS Microbiol. Lett. 174: 247-250 (1999) available from the National Center for Biotechnology Information, or by inspection.

The same types of similarity, or homology, can be obtained for nucleic acids by, for example, the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if similarity is found with at least one of these methods, the sequences would be said to have the stated similarity.

For example, as used herein, a sequence recited as having a particular percent similarity to another sequence refers to sequences that have the recited similarity as calculated by any one or more of the calculation methods described above. For example, a first sequence has 80 percent similarity, as defined herein, to a second sequence if the first sequence is calculated to have 80 percent similarity to the second sequence using the Zuker calculation method even if the first sequence does not have 80 percent similarity to the second sequence as calculated by any of the other calculation methods. As another example, a first sequence has 80 percent similarity, as defined herein, to a second sequence if the first sequence is calculated to have 80 percent similarity to the second sequence using both the Zuker calculation method and the Pearson and Lipman calculation method even if the first sequence does not have 80 percent similarity to the second sequence as calculated by the Smith and Waterman calculation method, the Needleman and Wunsch calculation method, the Jaeger calculation methods, or any of the other calculation methods. As yet another example, a first sequence has 80 percent similarity, as defined herein, to a second sequence if the first sequence is calculated to have 80 percent similarity to the second sequence using each of the calculation methods (although, in practice, the different calculation methods will often result in different calculated similarity percentages).

Each of the disclosed polypeptides can have one or more conservative amino acid substitutions. These conservative substitutions are such that a naturally occurring amino acid is replaced by one having similar properties. Such conservative substitutions do not alter the function of the polypeptide. For example, conservative substitutions can be made according to Table 4, shown below.

Thus, it is understood that, where desired, modifications and changes may be made in the nucleic acid encoding the polypeptides of this invention and/or in the amino acid sequence of the disclosed polypeptides and still obtain a polypeptide having like or otherwise desirable characteristics. Such changes may occur in natural isolates or may be synthetically introduced using site-specific mutagenesis, the procedures for which, such as mis-match polymerase chain reaction (PCR), are well known in the art. For example, certain amino acids may be substituted for other amino acids in a polypeptide without appreciable loss of functional activity. It is thus contemplated that various changes may be made in the amino acid sequence of the polypeptides of the present invention (or underlying nucleic acid sequence) without appreciable loss of biological utility or activity and possibly with an increase in such utility or activity.

The disclosed purified polypeptides can be used, for example, in vitro, as enzymes to catalyze chemical reactions for the purpose of degrading an organic material. Moreover, the disclosed polypeptides can be used on a large, industrial scale to degrade organic material. In one aspect, one or more purified polypeptides can be used to treat organic waste comprising, for example, methanol, formaldehyde, and/or ethanol, in order to clean up and detoxify a chemical spill that threatens the environment. The disclosed purified polypeptides can be used alone, or in any combination or sequence, to degrade organic material. Moreover, a person of skill would know which polypeptides to use and the effective amounts of each polypeptide to attain a selected end-product. For example, if a person of skill wanted to produce formaldehyde from methanol, only those polypeptides that comprise methanol dehydrogenase are selected. Further, if the goal is to degrade formaldehyde into a non-toxic end-product, for example in a toxic spill, a person of skill can choose the polypeptides that comprise formaldehyde-activating enzyme to initiate the process which will eventually result in the production of carbon dioxide. Thus, a person of skill can use the disclosed polypeptides in various combinations and sequences to degrade organic materials to prevent damage to land and water resources.

Further provided is a plurality of isolated nucleic acids that encode the disclosed purified polypeptides and variants or fragments thereof. Examples of nucleic acids that encode the disclosed polypeptides include the nucleic acids identified as SEQ ID NO:8, SEQ ID NO:9, SEQ ID NO:10, SEQ ID NO:11, SEQ ID NO:12, SEQ ID NO:14, SEQ ID NO:16, SEQ ID NO:18, SEQ ID NO:20, SEQ ID NO:24, SEQ ID NO:25, SEQ ID NO:26, SEQ ID NO:28, SEQ ID NO:30, SEQ ID NO:32, SEQ ID NO:38, SEQ ID NO:39, SEQ ID NO:40, SEQ ID NO:41, SEQ ID NO:42, SEQ ID NO:46, SEQ ID NO:47, and SEQ ID NO:50.

As used herein, the term "nucleic acid" refers to single or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the moieties discussed herein or may include alternative codons which encode the same amino acid as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides), a reduction in the AT content of AT rich regions, or replacement of non-preferred codon usage of the expression system to preferred codon usage of the expression system. The nucleic acid can be directly cloned into an appropriate vector, or if desired, can be modified to facilitate the subsequent cloning steps. Such modification steps are routine, an example of which is the addition of oligonucleotide linkers which contain restriction sites to the termini of the nucleic acid. General methods are set forth in Sambrook et al. (2001) Molecular Cloning—A Laboratory Manual (3rd ed.) Vol. 1-3, Cold Spring Harbor Laboratory, Cold Spring Harbor Press, NY, (Sambrook).

The nucleic acids of this invention can be detected with a probe capable of hybridizing to the nucleic acid of a cell or a sample. This probe can be a nucleic acid comprising the nucleotide sequence of a coding strand or its complementary strand or the nucleotide sequence of a sense strand or antisense strand, or a fragment thereof. The nucleic acid can comprise the nucleic acid of the bacterial genome, for Example the nucleic acid identified as SEQ ID NO:1, or fragments thereof. Thus, the probe of this invention can be either DNA or RNA and can bind either DNA or RNA, or both, in the biological sample.

The nucleic acids of the present invention, for example SEQ ID NO:8, SEQ ID NO:9, SEQ ID NO:10, SEQ ID NO:11, SEQ ID NO:12 or any of the other disclosed nucleic acid, and fragments thereof, can be utilized as probes or primers to detect nucleic acids of the disclosed bacterium. A polynucleotide probe or primer comprising at least 15 contiguous nucleotides can be utilized to detect a nucleic acid of the disclosed bacterium. Therefore, the polynucleotide probes or primers of this invention can be at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or at least 200 nucleotides in length.

As used herein, the term "nucleic acid probe" refers to a nucleic acid fragment that selectively hybridizes under stringent conditions with a nucleic acid comprising a nucleic acid set forth in a sequence listed herein. This hybridization must be specific. The degree of complementarity between the hybridizing nucleic acid and the sequence to which it hybridizes should be at least enough to exclude hybridization with a nucleic acid encoding an unrelated protein.

"Stringent conditions" refers to the washing conditions used in a hybridization protocol. In general, the washing conditions should be a combination of temperature and salt concentration chosen so that the denaturation temperature is approximately 5° C. to 20° C. below the calculated Tm of the nucleic acid hybrid under study. The temperature and salt conditions are readily determined empirically in preliminary experiments in which samples of reference DNA immobilized on filters are hybridized to the probe or polypeptide-coding nucleic acid of interest and then washed under conditions of different stringencies. The Tm of such an oligonucleotide can be estimated by allowing 20C for each A or T nucleotide, and 4° C. for each G or C. For example, an 18 nucleotide probe of 50% G+C would, therefore, have an approximate Tm of 54° C. Stringent conditions are known to one of skill in the art. See, for example, Sambrook et al. (2001). The following is an exemplary set of hybridization conditions and is not limiting:

Very High Stringency
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency
Hybridization: 6×SSC at RT to 55° C. for 16-20 hours
Wash at least twice: 2×-3×SSC at RT to 55° C. for 20-30 minutes each As mentioned above, the disclosed nucleic acids and fragments thereof can be utilized as primers to amplify a disclosed bacterial nucleic acid by standard amplification 30 techniques. A variety of PCR techniques are familiar to those skilled in the art. For a review of PCR technology, see White (1997) and the publication entitled "PCR Methods and Applications" (1991, Cold Spring Harbor Laboratory Press), which is incorporated herein by reference in its entirety for amplification methods. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188. Each of these publications is incorporated herein by reference in its entirety for PCR methods. One of skill in the art would know how to design and synthesize primers that amplify the disclosed nucleic acids or fragments thereof.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g., 32 P, 35 S, 3 H; etc. The label may be a two stage system, where the amplified DNA is conjugated to biotin, haptens, etc., having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, for example amplified fragment, can be analyzed by one of a number of methods known in the art. The nucleic acid can be sequenced by dideoxy or other methods. Hybridization with the sequence can also be used to determine its presence, by Southern blots, dot blots, etc.

Once the nucleic acid sequence is obtained, the sequence encoding the specific amino acids can be modified or changed at any particular amino acid position by techniques well known in the art. For example, PCR primers can be designed which span the amino acid position or positions and which can substitute any amino acid for another amino acid. Alternatively, one skilled in the art can introduce specific mutations at any point in a particular nucleic acid sequence through techniques for point mutagenesis. General methods are set forth in Smith, M. "In vitro mutagenesis" Ann. Rev. Gen., 19:423-462 (1985) and Zoller, M. J. "New molecular biology methods for protein engineering" Curr. Opin. Struct. Biol., 1:605-610 (1991), which are incorporated herein in their entirety for the methods. These techniques can be used to alter the coding sequence without altering the amino acid sequence that is encoded.

In another aspect, provided is a vector, comprising a disclosed nucleic acid. The vector can direct the in vivo or in vitro synthesis of any of the polypeptides described herein. The vector is contemplated to have the necessary functional elements that direct and regulate transcription of the inserted nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.). The vector, for example, can be a plasmid. The vectors can contain genes conferring hygromycin resistance, gentamicin resistance, or other genes or phenotypes suitable for use as selectable markers, or methotrexate resistance for gene amplification. The vector can comprise the nucleic acid in pET15b, pSRα-Neo, pPICZα, or pPIC9K.

There are numerous other E. coli (Escherichia coli) expression vectors, known to one of ordinary skill in the art, which are useful for the expression of the nucleic acid insert. Other microbial hosts suitable for use include bacilli, such as Bacillus subtilis, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences, for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures. Also, nucleic acid modifications can be made to promote amino terminal homogeneity.

Additionally, yeast expression can be used. The invention provides a nucleic acid encoding a polypeptide of the present invention, wherein the nucleic acid can be expressed by a yeast cell. More specifically, the nucleic acid can be expressed by Pichia pastoris or S. cerevisiae. There are several advantages to yeast expression systems, which include, for example, Saccharomyces cerevisiae and Pichia pastoris. First, evidence exists that proteins produced in a yeast secretion systems exhibit correct disulfide pairing. Second, efficient large scale production can be carried out using yeast expression systems. The Saccharomyces cerevisiae pre-pro-alpha mating factor leader region (encoded by the MFα-1 gene) can be used to direct protein secretion from yeast (Brake, et al.). The leader region of pre-pro-alpha mating factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha mating factor leader region. This construct can be put under the control of a strong transcription promoter, such as the alcohol dehydrogenase I promoter, alcohol oxidase I promoter, a glycolytic promoter, or a promoter for the galactose utilization pathway. The nucleic acid coding sequence is followed by a translation termination codon which is followed by transcription termination signals. Alternatively, the nucleic acid coding sequences can be fused to a second protein coding sequence, such as Sj26 or beta-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

In another aspect, provided are vectors containing the disclosed nucleic acids in a host suitable for expressing the nucleic acids. The host cell can be a prokaryotic cell, including, for example, a bacterial cell. In one aspect, the bacterial cell can be an isolated Gram-negative bacterium, wherein the bacterium is an aerobic, facultative methylotroph that produces colonies that are yellow pigmented, wherein the bacterium can use methanol as a sole carbon source and can oxidize glucose and ethanol into acid, and wherein the bacterium is designated Granulibacter bethesdensis and deposited under ATCC Accession No. BAA-1260. Moreover, the bacterial cell can be an E. coli cell.

Alternatively, the cell can be a eukaryotic cell, including, for example, a Chinese hamster ovary (CHO) cell, a mycloma cell, a Pichia cell, or an insect cell. The coding sequence for any of the polypeptides described herein can be introduced into a Chinese hamster ovary (CHO) cell line, for example, using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines have been developed and include myeloma cell lines, fibroblast cell lines, and a variety of tumor cell lines such as melanoma cell lines. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

Further provided is a method of making any of the disclosed purified polypeptides, fragments and variants described herein comprising culturing a host cell comprising a vector that encodes a polypeptide and purifying the polypeptide produced by the host cell. As mentioned above, these polypeptides include, but are not limited to, the polypeptides listed in Table 3, fragments thereof, polypeptides comprising an amino acid sequence at least about 95% similar to the disclosed amino acid sequences or fragments thereof and the purified polypeptides listed in Table 3, fragments thereof, with one or more conservative amino acid substitutions.

In another aspect, provided is a plurality of isolated antibodies, or fragments thereof, wherein each antibody, or fragment thereof, specifically binds to one of the disclosed polypeptides listed in Table 3. Thus, provided is an isolated antibody, or fragment thereof, that specifically binds, for example, a purified polypeptide identified as SEQ ID NO:3, or a fragment thereof. Another example of an isolated antibody, or fragment thereof, is an antibody that specifically binds to a purified polypeptide identified as SEQ ID NO:4.

In one aspect, provided is an isolated antibody, or fragment thereof, that specifically binds an epitope contained within each polypeptide listed in Table 3. In other words, provided is a plurality of isolated antibodies, or fragments thereof, that specifically bind an epitope contained within each amino acid sequence of the polypeptides disclosed in Table 3.

An antibody of the present invention can be a polyclonal antibody or a monoclonal antibody. By "specifically binds" is meant an antibody binding reaction which is determinative of the presence of the antigen (in the present case, each polypeptide listed in Table 3, or antigenic fragments thereof) among a heterogeneous population of polypeptides and other biologics. Thus, under designated immunoassay conditions, the specified antibodies bind preferentially to a particular polypeptide and do not bind in a significant amount to other polypeptides in the sample. Preferably, specific binding includes binding at about or above 1.5 times assay background, and the absence of significant binding is less than 1.5 times assay background.

Preferably, the antibody binds a disclosed polypeptide ex vivo or in vivo. Optionally, the antibody of the invention is labeled with a detectable moiety. For example, the detectable moiety can be selected from the group consisting of a fluorescent moiety, an enzyme-linked moiety, a biotin moiety and a radiolabeled moiety. The antibody can be used in techniques or procedures such as diagnostics, screening, or imaging. Anti-idiotypic antibodies and affinity matured antibodies are also considered to be part of the invention. Thus, an antibody disclosed herein can be used to detect the presence of *Granulibacter bethesdensis* in a biological sample from a subject, for example a lymph node removed from the subject, in order to diagnose the cause of an infection.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse or other species. The heavy chain constant domains that correspond to the different classes of immunoglobulins are called alpha, delta, epsilon, gamma, and mu, respectively.

As used herein, the terms "immunoglobulin heavy chain or fragments thereof" and "immunoglobulin light chain or fragments thereof" encompass chimeric peptides and hybrid peptides, with dual or multiple antigen or epitope specificities, and fragments, including hybrid fragments. Thus, fragments of the heavy chains and/or fragments of the light chains that retain the ability to bind their specific antigens are provided.

In another aspect, provided is a method of degrading an organic material, comprising contacting the organic material with an effective, degrading amount of an isolated Gram-negative bacterium, wherein the bacterium is an aerobic, facultative methylotroph that produces colonies that are yellow pigmented, wherein the bacterium can use methanol as a sole carbon source and can oxidize glucose and ethanol into acid, whereby contacting the organic material with the bacterium degrades the organic material. As used herein "degrade" means "to break down" or "to decompose." As used herein, "biodegrade" means "to break down or decompose by biological processes." Thus, the process of decomposing an organic material by contacting the material with bacteria is an example of biodegradation. As used herein, an "effective amount" is within the knowledge of one skilled in the art. Various methods are known by which a person of skill can determine the amount of bacteria required to effectively degrade the organic material, e.g., organic waste, of interest. The organic material can comprise any composition containing carbon and includes, but is not limited to, methanol, formaldehyde, ethanol, hydrocarbons, benzene, and other aldehydes, including intermediate breakdown products of the materials disclosed herein. In one aspect, the bacterium comprises a genome identified as SEQ ID NO:1 and is deposited under GenBank Accession No. CP000394. In another aspect, the bacterium comprises a 16SRNA nucleic acid that is greater than about 98% similar to the nucleic acid identified as SEQ ID NO:2. In yet another aspect, the bacterium comprises a 16SRNA nucleic acid that is greater than about 99% similar to the nucleic acid identified as SEQ ID NO:2. In one aspect, the bacterium comprises a 16SRNA nucleic acid identified as SEQ ID NO:2.

The contacting step of the disclosed method occurs at a pH of from about 5.0 to about 7.5. In one aspect, the contacting step occurs at a pH of from about 5.5 to about 6.5. The method disclosed can be carried out at a temperature from about 15° C. to about 40° C. In another aspect, the disclosed method can be carried out at a temperature from about 25° C. to about 37° C.

Further provided is a method of growing an isolated Gram-negative bacterium, designated *Granulibacter bethesdensis* and deposited under ATCC Accession No. BAA-1260, wherein the bacterium is an aerobic, facultative methylotroph that produces colonies that are yellow pigmented, wherein the bacterium can use methanol as a sole carbon source and can oxidize glucose and ethanol into acid, comprising culturing the bacterium at a temperature and on a medium effective to promote growth of the bacterium. The bacterium can grow at a temperature from about 30° C. to about 37° C. In one aspect, the bacterium can grow at a temperature from about 35° C. to about 37° C. Further, the bacterium can grow on medium wherein the pH is from about 5.0 to about 7.5. In one aspect, the pH of the medium can be from about 5.5 to about 6.5. Media are currently known that are effective in promoting growth of the disclosed bacterium. Therefore, a person of skill would know which media would be effective in promoting the growth of the novel bacterium. Examples of media on which the bacterium can grow are shown below in Example 3.

With the need for alternative sources of energy becoming of paramount importance, biofuel cells potentially offer many solutions to our power problems. Biofuel cells can utilize readily available substrates, for example glucose, ethanol, methanol, and formaldedyde and convert them into electrical energy and benign by-products. As used herein, a "biofuel cell" is a small energy storage and conversion device that can provide a remote power source exactly where it is needed and only when needed. In one aspect, a biofuel cell can comprise whole bacteria that serve as small bioreactors to produce energy. Alternatively, a person of skill can isolate the polypeptide enzymes from the bacteria and/or produce them as taught herein for use in a biofuel cell and thus obviate the need for using the live bacterium.

The electrochemical oxidation of fuels can be biocatalyzed by enzymes that communicate electrically with electrodes. There are different classes of oxidative enzymes (e.g., dehydrogenases) that can be used to establish electrical communication. *G. bethesdensis* contains many of these enzymes that alone or in combination can be used for power generation.

For example, *Granulibacter bethesdensis* can use methanol as a sole carbon source in a biofuel cell. In such an enzymatic fuel cell, an anode chamber contains an enzyme (polypeptide) or combination of enzymes, a substrate, for example, methanol, and a mediator. An enzyme, or combination of enzymes, can oxidize the substrate and release electrons to the anode using the mediator.

In one aspect, a biofuel cell utilizes the nicotinamide redox co-factors NAD+ and NADP+. These cofoactors play important roles in biological electron transport. They are carriers of electrons and can activate the biocatalytic functions of dehydrogenases. For example, a methanol biofuel cell uses enzymes in the conversion of methanol into carbon dioxide using the NAD+-dependent alcohol dehydrogenase, an aldehyde dehydrogenase and formate dehydrogenase. All of these enzymes are in *Granulibacter bethesdensis*. When these enzymes are coupled with an enzyme diaphorase, NADH is oxidized to NAD+ using an electron acceptor which is present in the anode. The biocatalytic anode is then conjugated with an oxygen-containing cathode to complete the biofuel cell.

Other mediators of oxidation can be used such as pyrroloquinoline quinone (PQQ) in a biofuel cell. For example, one of the main enzymes used by *G. bethesdensis* to convert methanol into formaldehyde is methanol dehydrogenase, a PQQ-dependent enzyme that can be used in an enzymatic fuel cell. In one aspect, key enzymes involved in oxidative pathways can be immobilized onto membranes which contact an organic substrate, for example methanol, formaldehyde, or ethanol, to produce energy. Examples of materials known in the art for use in making such membranes include, but are not limited to, graphite and polymers, for example nafion.

Therefore, provided is a biofuel cell, comprising a cathode, an anode, a conductive medium, an ion exchange membrane interposed between the cathode and the anode, and a bacterial catalyst around the anode, wherein the bacterial catalyst comprises an isolated Gram-negative bacterium, wherein the bacterium is an aerobic, facultative methylotroph that produces colonies that are yellow pigmented, wherein the bacterium can use methanol as a sole carbon source and can oxidize glucose and ethanol into acid. An example of the bacterium is *Granulibacter bethesdensis*, having the ATCC patent deposit designation BAA-1260. Exemplary uses for a biofuel cell include, but are not limited to, uses in cell phones, computers (e.g., laptops), remote sensors, or in-body implants such as pacemakers, medical sensing, or drug dispersal devices. A miniature biofuel cell comprising the disclosed bacterium can convert stored energy in organic materials to electrical energy and power.

In another aspect, provided is a method of converting chemical energy in an organic material into electrical energy comprising contacting the organic material with an effective amount of a bacterial catalyst comprising an isolated Gram-negative bacterium, wherein the bacterium is an aerobic, facultative methylotroph that produces colonies that are yellow pigmented, wherein the bacterium can use methanol as a sole carbon source and can oxidize glucose and ethanol into acid. In one aspect, the method can be carried out by a bacterium designated *Granulibacter bethesdensis*, having the ATCC patent deposit designation BAA-1260.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Microbiology

The growth of the isolate was assessed on various media under different incubation conditions. The organism grew best at 35° C. on *Acetobacter* Medium [20] with the following modifications: glucose (50.0 g/L), CaCO3 (12.5 g/L), autolyzed yeast (5.0 g/L), agar.(15.0 g/L). Colonies growing on this modified *Acetobacter* Medium developed a yellow color after 5 days. Good growth after 4-5 days of incubation was also obtained on BCYE agar and on tryptic soy agar (TSA) with sheep blood (Remel). Growth was not improved in a CO2 atmosphere.

Commercial biochemical kits, supplementary phenotypic tests and sequencing were used to identify the isolate. Commercial kits used included the API 20 NE (BioMerieux, Durham, N.C.) and the RapID NH (Remel, Lenexa, Kans.). Additional phenotypic tests included oxidase, catalase, oxidative-fermentative (OF) medium with different sugars (OF medium King, Remel), lysine and ornithine decarboxylases, arginine dihydrolase, urease test (Rapid Urea Slant, Hardy Diagnostics), and motility. Susceptibility testing was performed on TSA with sheep blood by the E-test (Amersham Biosciences Biodisk, Piscataway, N.J.). Sequencing and phylogenetic analysis. The full 16S rRNA gene was sequenced using the MicroSeq Full Gene 16S rRNA Bacterial Isolation Sequencing Kit (Applied Biosystems, Foster City, Calif.), according to the manufacturer's protocol, and sequences were analyzed using the 3100 Genetic Analyzer (Applied Biosystems). The Lasergene program (version 5.51; DNASTAR, Inc. Madison, Wis.) was used for sequence assembly and alignment. The assembled 16S rDNA sequence from the patient isolate was compared with 16S rDNA sequences available in GenBank databases using the standard nucleotide-nucleotide Basic Local Alignment Search Tool (Blastn) program (National Center for Biotechnology Information, Bethesda, Md.). Multiple sequence alignments of the 16S rRNA gene sequences from the isolate and the closest GenBank matches were done by the CLUSTAL W method.

Phylogenetic analyses were performed with the PHYLIP version 3.5c package [21]. Distance matrices based on Kimura's two-parameter model were produced with DNADIST program, and a neighbor-joining tree constructed with the NEIGHBOR program. The resulting unrooted tree was depicted using the TreeView version 1.4 package [22].

The 16S rDNA sequence from this novel gram-negative rod was deposited in GenBank under accession number AY788950.

Immunology Studies

Preparation of Protein Extracts, SDS Gel Electrophoresis, and Western-Blot Analysis. Bacterial cells were pelleted by centrifugation and extracted with the Pierce (Rockford, Ill.) bacterial protein extraction reagent. Protein concentrations were determined using the Pierce protein assay. 2 µg of total protein per lane were electrophoresed on 10% SDS-PAGE, and the separated proteins transferred to PVDF membrane (Invitrogen Life Technologies, Carlsbad, Calif.). The membrane was blocked in TBS buffer containing 5% non-fat dried milk and 0.05% Tween-20 before incubation with human or mouse serum (1:100 to 1:100,000 dilution). After 3 washes, the membrane was incubated with horseradish peroxidase conjugated goat anti-human or goat anti-mouse IgG (1:10000 to 1:20000; Amersham Biosciences). The blots were developed using the enhanced chemiluminescence kit (ECL Plus; Amersham Biosciences) as described by the manufacturer.

Example 2

To characterize the novel organism, a polyphasic taxonomic approach was taken, using phenotypic data in the form of biochemical tests and a multilocus DNA sequence analysis for phylogenetic reconstruction. For the multilocus approach, (1) the 16S rRNA gene, (2) the Internal Transcribed Spacer (ITS) region and (3) the RecA protein were studied. The first two loci have been used extensively in the phylogenetic analysis of the Acetobacteraceae [47, 43, 40, 39], while the RecA protein has been described as a model molecule for systematic studies between related species in the alpha-proteobacteria, generally producing results congruent with those obtained from 16S data [30]. The results of the study indicate that the bacterium is most appropriately placed in a new genus within the acetic acid bacteria.

Phenotypic Analysis

Phenotypic identification was initially attempted with commercial biochemical kits and supplementary phenotypic tests routinely used in clinical microbiology. Kits included the API 20 NE (BioMerieux, Durham, N.C.) and the RapID NH (Remel, Lenexa, Kans.), neither of which yielded an identification. Supplementary phenotypic tests included oxidase, catalase, oxidative-fermentative (OF) medium with either glucose, lactose, mannitol, sucrose, maltose or xylose (OF medium King, Remel), lysine and ornithine decarboxylases (Remel), arginine dihydrolase (Remel), urease (Rapid Urea Slant, Hardy Diagnostics), and motility (Motility Test Medium, Hardy Diagnostics). Growth on methanol as a sole carbon source was performed on medium 569 [45]. Additional tests used for the acetic acid bacteria (Table 1) as well morphological and physiological characterization were carried out as previously described [44, 25]. Cellular fatty acid analysis was performed as described elsewhere [49].

DNA Isolation and Sequencing

DNA was isolated from using the NucliSens kit (bioMerieux, USA). The 16S gene was initially PCR-amplified and sequenced using the MicroSeq Full Gene 16S rRNA Bacterial Isolation Sequencing Kit (Applied Biosystems, Foster City, Calif.), according to the manufacturer's protocol. Sequences were analyzed using the 3100 Genetic Analyzer (Applied Biosystems). The Lasergene program (version 5.51; DNASTAR, Inc. Madison, Wis.) was used for sequence assembly and alignment. 16S rDNA sequences from the isolates were compared with 16S rDNA sequences available in GenBank/EMBL/DDBJ databases. Preliminary whole genome sequencing efforts for G. bethesdensis were performed by methods used for several other bacteria [29, 37, 35]. The 16S rRNA gene, the ITS region, and the RecA protein encoding gene were collected by Blast searching the preliminary genome assembly.

Phylogenetic Analysis

Nucleotide and deduced amino acid sequences for targeted genes were initially analyzed with MacVector version 6.0/7.0 software package (Oxford Molecular, Beaverton, Oregon). DNA sequences were first aligned with the ClustalW program in the Lasergene software package (DNASTAR, Madison, Wisc.). Alignments for the 16S rRNA gene, ITS region and the RecA sequences were performed following standard procedures provided by the manufacturer (DNASTAR, Madison, Wisc.). The alignments were transferred into the MacClade program (Maddison, D. R. and W. P. Maddison, 2003. MacClade 4: Analysis of phylogeny and character evolution. Version 4.06. Sinauer Associates, Sunderland, Mass.) for removal of insertions/deletions (indels), sequence errors, equalizing sequence lengths and manual correction of the alignments. MacClade output files were opened in PAUP (Swofford, D. L. 1998. PAUP*. Phylogenetic analysis using parsimony (*and other methods). Version 4. Sinauer Associates, Sunderland, Mass.) with an 'include all' line command. For the 16S rRNA gene, ITS region, and RecA protein, maximum likelihood neighbor-joining trees were created with a paraphyletic outgroup. The robustness of clade designations was tested with a full heuristic search and 1000 bootstrap replicates.

Nucleotide Sequence Accession Numbers

Nucleotide sequences for the 16S rRNA gene, ITS region and recA gene for G. bethesdensis have been deposited in the GenBank database under the following accession numbers: AY788950, DQ340304 and DQ340305, respectively. The nucleotide sequence for the Rhodospirillum rubrum ITS region was obtained from the R. rubrum genome project of the US Department of Energy Joint Genome Institute.

Results

Phenotypic Analysis

Isolates of this bacterium were obtained from lymph node cultures of a subject with CGD. The organism was a Gram-negative coccobacillus to rod, and obligately aerobic. On initial isolation from the subject, colonies were visible after 4-6 days of incubation on buffered charcoal yeast extract (3CYE) agar, Sabouraud dextrose agar, inhibitory mold agar and Middlebrook 7H11 agar incubated in either ambient air at 30° C. or 7% CO2 at 35° C. A second isolate grew after two weeks in a commercial broth used for the isolation of mycobacteria (BD Bactec MGIT 960, Becton, Dickinson and Company, Sparks, Maryland). A third isolate grew after five days on BCYE agar.

As part of the characterization of this novel bacterium, different media commercially available and made in the laboratory were evaluated. The organism grew optimally on a modified glucose-yeast extract-CaCO3 *Acetobacter* medium (Atlas, R. M., 1993) containing: glucose (50.0 g/L), CaCO3 (12.5 g/L), autolyzed yeast (5.0 g/L), and agar (15.0 g/L). Colonies on this medium were convex, entire and smooth and produced a yellow non-diffusible pigment. The organism grew in a temperature range of 25-37° C. within four days, with an optimal temperature of 35-37° C. There was no growth at 42° C. Optimal pH range for growth was 5.0-6.5.

The organism was non-motile, catalase-positive and oxidase-negative. Lysine and ornithine decarboxylases and arginine dihydrolase were all negative. Urease was positive for two isolates, and weak or negative for the third isolate; there was weak acid production from glucose but no acid production from lactose, mannitol, sucrose, maltose or xylose. The bacterium grew on glutamate and mannitol agars. It oxidized lactate and acetate to carbon dioxide and water, but the activity of the latter was weak. For testing ketogenic activity on glycerol (dihydroxyacetone production), glucose 1 g/l was added to the glycerol medium because the organism failed to grow on the medium described by Shimwell et al. 1960. The bacterium did not produce dihydroxyacetone from glycerol. The organism grew on methanol as a sole carbon source. It generated acetic acid poorly on ethanol-CaCO3 agar (with 2% CaCO3) [25]. Acetic acid production was more evident on modified ethanol-CaCO3 agar plates containing lower concentrations of CaCO3. The results of these and additional biochemical tests are summarized in Table 1.

The major fatty acids of the bacterium were a straight-chain unsaturated acid (18:1w7c) and C16:0, which accounted for 50 and 17% of the total cellular fatty acids, respectively. Other fatty acids identified were C19:0cyc11-12 (10%), and smaller amounts of 2-OH C14:0, sum of 3-OH C14:0 and/or i-C16:1I, 3-OH C16:0, C17:0, C17:1w6c, C18:0, 2-OH C18:1, 2-OH C16:0, C16:1w7c, and 3-OH C18:0.

Multi-Locus DNA Sequence Analysis 16S rRNA Gene

A multilocus approach was used for the phylogenetic characterization of the novel bacterium. During genome sequencing efforts, 3 homologous 16S-23S rRNA gene loci were discovered. The 16S rRNA gene is 1482 bases in length and identical at all three loci. Blast searches indicated that the 16S rRNA gene sequence was most similar to sequences of other organisms in the family Acetobacteraceae. Because 16S rRNA gene sequences are of varying lengths in the database, ClustalW alignments were used to identify a conserved, common, internal 1401 base pair region, among multiple representatives of the Acetobacteraceae. This region spanned positions 33 to 1434 of the 16S rRNA gene of the novel bacterium. Sixteen 16S gene sequences of representative taxa or type strains within the family Acetobacteraceae were collected from NCBI and the resulting phylogenetic tree is shown in FIG. 1. Multiple iterations of 16S analyses were performed with many different species and strains of the Acetobacteraceae with no strains homologous to the novel bacterium detected. Phylogenetic groupings of representatives of the *Acetobacter, Gluconobacter, Gluconacetobacter, Acidomonas, Asaia* and *Kozakia* genera, as seen in FIG. 1 are similar to what has previously been published [47, 52, 53]. The 16S rRNA gene sequence of the novel organism groups within the Acetobacteraceae family, while branch length and positioning indicates that it warrants separate genus-level status (FIG. 1). Percent identity values for our bacterium compared with representative members of the Acetobacteraceae from 95.6% with *Gluconacetobacter* liquefaciens to 86.2% with *Stella humosa* (Table 2).

ITS Region

Phylogenetic analysis has been performed on *Gluconobacter* using both the 16S rRNA gene sequence and the internal transcribed spacer (ITS) region for comparison [47] and on ITS alone [52, 53]. The ITS sequence of our bacterium is 776 bases in length and identical at all three ribosomal loci. Given the variant lengths of ITS sequences in the database, a conserved internal 752 base-pair region from the ITS sequence of the novel organism, spanning base positions 24 to 776, was chosen for further phylogenetic analysis. Similar regions from 14 representative taxa (including eight type strains), with a focus on the acetic acid bacteria, were collected from GeneBank for analysis. The resulting phylogenetic tree is shown in FIG. 1. The grouping and associations seen in FIG. 1 for the *Acetobacter, Gluconobacter* and *Gluconoacetobacter* species are compatible with previously published results for the ITS region of these species [47, 52, 53]. In addition, the ITS sequence of the novel organism demonstrates distances from these species that were apparent in the genus-level analysis. The results confirm that the ITS region in the Acetobacteraceae is well suited to comparative analysis with the 16S rRNA gene, as previously demonstrated [47, 52, 53]. Branch length (substitutions/site) and branching pattern indicate that the organism should be classified in a separate genus within the family Acetobacteraceae. Percent similarity values of the ITS region of the isolate ranged from 56.2% with *Acetobacter aceti* to 45.1% with *R. rubrum*.

RecA Protein

The RecA protein, in addition to the 16S rRNA gene and the ITS region, has been used in multilocus sequence analysis for taxonomic studies of novel bacterial isolates [30]. The recA gene sequences are the only protein encoding gene sequences that are publicly available in databases for organisms in the genera *Acetobacter, Gluconobacter* and *Gluconoacetobacter*. While a protein-encoding locus such as TecA is subject to different functional selective pressures than the 16S rRNA gene or ITS sequences [38], recA is considered a conserved gene and is suitable for multilocus phylogenetic analyses [38]. The recA gene of the novel isolate is 1053 bases in length and translates into 351 amino acids. Most Acetobacteraceae recA genes or proteins in the database are partial sequences; therefore, 152 amino acids encoded in 456 conserved nucleotides, spanning residues 407 to 863 in the recA gene of our organism, were studied. The results for 12 RecA sequences, including those for 6 type strains, with a focus again on the acetic bacteria were similar to what was seen for the ITS and 16S regions. Branching pattern and length again suggest separate genus-level status for the novel organism within the family Acetobacteraceae. DNA similarities for the recA gene of the novel organism ranged from 80.6% with *Acetobacter estunensis* to 71.4% for

*Rhodobacter sphaeroides*, while RecA protein similarities ranged from 90.8% with *Acetobacter orleanensis* to 75.0% with *R. sphaeroides*.

Example 3

Media on Which the Novel Bacterium Grows

Medium #1

| Medium 569 (Methanol minimal agar) | |
|---|---|
| KNO3 | 1.0 g |
| MgSO4•7H2O | 0.2 g |
| CaCl2•2H2O | 0.02 g |
| Na2HPO4 | 0.23 g |
| NaH2PO4 | 0.07 g |
| FeSO4•7H2O | 1.0 mg |
| CuSO4•5H2O | 5.0 mg |
| H3BO3 | 10.0 mg |
| MnSO4•5H2O | 10.0 mg |
| ZnSO4•7H2O | 70 mg |
| MoO3 | 10.0 mg |
| Agar | 15.0 g |
| Distilled water | 990 ml |
| Methanol | 10 ml |

Medium #2

The organism grew optimally on a modified glucose-yeast extract-CaCO3 *Acetobacter* medium (Atlas, R. M., 1993) containing: glucose (50.0 g/L), CaCO3 (12.5 g/L), autolyzed yeast (5.0 g/L), and agar (15.0 g/L).

References

1. Segal B H, Leto T L, Gallin J I, Malech H L, Holland S M (2000) Genetic, biochemical, and clinical features of chronic granulomatous disease. Medicine (Baltimore) 79: 170-200.
2. Winkelstein J A, Marino M C, Johnston R B, Jr., Boyle J, Curnutte J, et al. (2000) Chronic granulomatous disease. Report on a national registry of 368 patients. Medicine (Baltimore) 79: 155-169.
3. Dorman S E, Guide S V, Conville P S, DeCarlo E S, Malech H L, et al. (2002) *Nocardia* infection in chronic granulomatous disease. Clin Infect Dis 35: 390-394.
4. Guide S V, Stock F, Gill V J, Anderson V L, Malech H L, et al. (2003) Reinfection, rather than persistent infection, in patients with chronic granulomatous disease. J Infect Dis 187: 845-853.
5. Sereti I, Holland S M (2001) Disseminated nocardiosis in a patient with X-linked chronic granulomatous disease and human immunodeficiency virus infection. Clin Infect Dis 33: 235-239.
6. Speert D P, Bond M, Woodman R C, Curnutte J T (1994) Infection with *Pseudomonas cepacia* in chronic granulomatous disease: role of nonoxidative killing by neutrophils in host defense. J Infect Dis 170: 1524-1531.
7. Lekstrom-Himes J A, Holland S M, DeCarlo E S, Miller J, Leitman S F, et al. (1994) Treatment with intralesional granulocyte instillations and interferon-gamma for a patient with chronic granulomatous disease and multiple hepatic abscesses. Clin Infect Dis 19: 770-773.
8. Koch R (1882) Die Atiologie der Tuberkulose. Berliner Klinische Wochenschrift 19: 221-230.
9. Stackebrandt E (2003) The Richness of Prokaryotic Diversity: There Must Be a Species Somewhere. Food Technol Biotechnol 41: 17-22.
10. Poblet M, Rozes N, Guillamon J M, Mas A (2000) Identification of acetic acid bacteria by restriction fragment length polymorphism analysis of a PCR-amplified fragment of the gene coding for 16S rRNA. Lett Appl Microbiol 31: 63-67.
11. Lisdiyanti P, Kawasaki H, Seki T, Yamada Y, Uchimura T, et al. (2001) Identification of *Acetobacter* strains isolated from Indonesian sources, and proposals of *Acetobacter syzygii* sp. nov., *Acetobacter cibinongensis* sp. nov., and *Acetobacter orientalis* sp. nov. J Gen Appl Microbiol 47: 119-131.
12. Seearunruangchai A, Tanasupawat S, Keeratipibul S, Thawai C, Itoh T, et al. (2004) Identification of acetic acid bacteria isolated from fruits collected in Thailand. J Gen Appl Microbiol 50: 47-53.
13. Yamada Y, Hosono R, Lisdyanti P, Widyastuti Y, Saono S, et al. (1999) Identification of acetic acid bacteria isolated from Indonesian sources, especially of isolates classified in the genus *Gluconobacter*. J Gen Appl Microbiol 45: 23-28.
14. Sievers M, Schlegel H G, Caballero-Mellado J, Dobereiner J, Ludwig W (1998) Phylogenetic identification of two major nitrogen-fixing bacteria associated with sugarcane. Syst Appl Microbiol 21: 505-508.
15. Bartowsky E J, Xia D, Gibson R L, Fleet G H, Henschke P A (2003) Spoilage of bottled red wine by acetic acid bacteria. Lett Appl Microbiol 36: 307-314.
16. Gonzalez A, Hierro N, Poblet M, Rozes N, Mas A, et al. (2004) Application of molecular methods for the differentiation of acetic acid bacteria in a red wine fermentation. J Appl Microbiol 96: 853-860.
17. Sokollek S J, Hertel C, Hammes W P (1998) Description of *Acetobacter oboediens* sp. nov. and *Acetobacter pomorum* sp. nov., two new species isolated from industrial vinegar fermentations. Int J Syst Bacteriol 48 Pt 3: 935-940.
18. Nanda K, Taniguchi M, Ujike S, Ishihara N, Mori H, et al. (2001) Characterization of acetic acid bacteria in traditional acetic acid fermentation of rice vinegar (komesu) and unpolished rice vinegar (kurosu) produced in Japan. Appl Environ Microbiol 67: 986-990.
19. Snyder R W, Ruhe J, Kobrin S, Wasswestein A, Doline C, et al. (2004) Asaia bogorensis peritonitis identified by 16S ribosomal RNA sequence analysis in a patient receiving peritoneal dialysis. Am J Kid Dis 44:E15-E17.
20. Atlas R M (1993) Handbook of Microbiological Media. Boca Raton: CRC Press.
21. Felsenstein J (1993) PHYLIP (Phylogeny Inference Package). 3.5c ed.
22. Page R (1996) Tree View: an application to display phylogenetic trees on personal computers. Comput Appl Biosci 12: 357-358.
23. Jackson S H, Gallin J I, Holland S M (1995) The p47phox mouse knock-out model of chronic granulomatous disease. J Exp Med 182: 751-758.
24. Pollock J D, Williams D A, Gifford M A, Li L L, Du X, et al. (1995) Mouse model of X-linked chronic granulomatous disease, an inherited defect in phagocyte superoxide production. Nat Genet 9: 202-209.
25. Asai, T., Iizuka, H. and Komagata, K. (1964). The flagellation and taxonomy of genera *Gluconobacter* and *Acetobacter* with reference to the existence of intermediate strains, J Gen Appl Microbiol 10, 95-126.
26. Bartual, S. G., Seifert, H., Hippler, C., Luzon, M. A., Wisplinghoff, H. and Rodriguez-Valera, F. (2005). Development of a multilocus sequence typing scheme for characterization of clinical isolates of *Acinetobacter baumannii*, J Clin Microbiol 43, 4382-4390.

27. Boesch, C., Trcek, J., Sievers, M. and Teuber, M. (1998). *Acetobacter intermedius*, sp. nov, Syst Appl Microbiol 21, 220-229.
28. Cleenwerck, I., Vandemeulebroecke, K., Janssens, D., Swings, J. (2002). Re-examination of the genus *Acetobacter*, with descriptions of *Acetobacter cerevisiae* sp. nov. and *Acetobacter malorum* sp. nov, Int J Syst Evol Microbiol 52, 1551-1558.
29. DelVecchio, V. G., Kapatral, V., Redkar, R. J., Patra, G., Mujer, C., Los, T., Ivanova, N., Anderson, I., Bhattacharyya, A., Lykidis, A., Reznik, G., Jablonski, L., Larsen, N., D'Souza, M., Bernal, A., Mazur, M., Goltsman, E., Selkov, E., Elzer, P. H., Hagius, S., O'Callaghan, D., Letesson, J. J., Haselkom, R., Kyrpides, N. and Overbeek, R. (2002). The genome sequence of the facultative intracellular pathogen *Brucella melitensis*, Proc Natl Acad Sci USA 99, 443-448.
30. Eisen, J. A. (1995). The RecA protein as a model molecule for molecular systematic studies of bacteria: comparison of trees of RecAs and 16S rRNAs from the same species, J Mol Evol 41, 1105-1123.
31. Franke, I. H., Fegan, M., Hayward, C., Leonard, G., Stackebrandt, E. and Sly, L. I. (1999). Description of *Gluconacetobacter sacchari* sp. nov., a new species of acetic acid bacterium isolated from the leaf sheath of sugar cane and from the pink sugar-cane mealy bug, Int J Syst Bacteriol 49 Pt 4, 1681-1693.
32. Garcia-Martinez, J., Acinas, S. G., Anton, A. I. and Rodriguez-Valera, F. (1999). Use of the 16S-23S ribosomal genes spacer region in studies of Prokaryotic diversity, J Microbiol Methods 36, 54-64.
33. Gevers, D., Cohan, F. M., Lawrence, J. G., Spratt, B. G., Coenye, T., Feil, E. J., Stackebrandt, E., Van de Peer, Y., Vandamme, P., Thompson, F. L. and Swings, J. (2005). Opinion: Re-evaluating prokaryotic species, Nat Rev Microbiol 3, 733-739.
34. Greenberg, D. E., Ding, L., Zelazny, A. M., Stock, F., Wong, A., Anderson, V. L., Miller, G., Kleiner, D. E., Tenorio, A. R., Brinster, L., Dorward, D. W., Murray, P. R. and Holland, S. M. A novel bacterium associated with lymphadenitis in a patient with chronic granulomatous disease, PloS Pathogens (in press).
35. Ivanova, N., Sorokin, A., Anderson, I., Galleron, N., Candelon, B., Kapatral, V., Bhattacharyya, A., Reznik, G., Mikhailova, N., Lapidus, A., Chu, L., Mazur, M., Goltsman, E., Larsen, N., D'Souza, M., Walunas, T., Grechkin, Y., Pusch, G., Haselkorn, R., Fonstein, M., Ehrlich, S. D., Overbeek, R. and Kyrpides, N. (2003). Genome sequence of *Bacillus cereus* and comparative analysis with *Bacillus anthracis*, Nature 423, 87-91.
36. Jojima, Y., Mihara, Y., Suzuki, S., Yokozeki, K., Yamanaka, S. and Fudou, R. (2004). *Saccharibacter floricola* gen. nov., sp. nov., a novel osmophilic acetic acid bacterium isolated from pollen, Int J Syst Evol Microbiol 54, 2263-2267.
37. Kapatral, V., Anderson, I., Ivanova, N., Reznik, G., Los, T., Lykidis, A., Bhattacharyya, A., Bartman, A., Gardner, W., Grechkin, G., Zhu, L., Vasieva, O., Chu, L., Kogan, Y., Chaga, O., Goltsman, E., Benal, A., Larsen, N., D'Souza, M., Walunas, T., Pusch, G., Haselkorn, R., Fonstein, M., Kyrpides, N. and Overbeek, R. (2002). Genome sequence and analysis of the oral bacterium *Fusobacterium nucleatum* strain ATCC 25586, J Bacteriol 184, 2005-2018.
38. Liiv, A., Tenson, T., Margus, T. and Remme, J. (1998). Multiple functions of the transcribed spacers in ribosomal RNA operons, Biol Chem 379, 783-793.
39. Lisdiyanti, P., Kawasaki, H., Seki, T., Yamada, Y., Uchimura, T., Komagata, K. (2000). Systematic study of the genus *Acetobacter* with descriptions of *Acetobacter indonesiensis* sp. nov., *Acetobacter tropicalis* sp. nov., *Acetobacter orleanensis* (Henneberg 1906) comb. nov., *Acetobacter lovaniensis* (Frateur 1950) comb. nov., and *Acetobacter estunensis* (Carr 1958) comb. nov, J Gen Appl Microbiol 46, 147-165.
40. Lisdiyanti, P., Kawasaki, H., Widyastuti, Y., Saono, S., Seki, T., Yamada, Y., Uchimura, T. and Komagata, K. (2002). *Kozakia baliensis* gen. nov., sp. nov., a novel acetic acid bacterium in the alpha-proteobacteria, Int I Syst Evol Microbiol 52, 813-818.
41. Ludwig, W., Strunk, O., Klugbauer, S., Klugbauer, N., Weizenegger, M., Neumaier, J., Bachleitner, M. and Schleifer, K. H. (1998). Bacterial phylogeny based on comparative sequence analysis, Electrophoresis 19, 554-568.
42. Owen, R. J. (2004). Bacterial Taxonomics: Finding the Wood Through the Phylogenetic Trees. In Genomics, Proteomics, and Clinical Bacteriology: Methods and Reviews, pp. 353-384. Edited by Neil Woodford and Alan P. Johnson London, UK: Humana Press.
43. Ruiz, A., Poblet, M., Mas, A., Guillamon, J. M. (2000). Identification of acetic acid bacteria by RFLP of PCR-amplified 16S rDNA and 16S-23S rDNA intergenic spacer, Int J Syst Evol Microbiol 50, 1981-1987.
44. Shimwell, J. L., Carr, J. G. and Rhodes, M. E. (1960). Differentiation of *Acetomonas* and *Pseudomonas*., J Gen Microbiol 23, 283-286.
45. Sievers, M., Swings, J. (2005). Family Acetobacteraceae. Genus *Acidomonas*. In Bergey's Manual of Systematic Bacteriology, page 68. Edited by George M. Garrity. Springer.
46. Sievers, M., Gaberthuel, C., Boesch, C., Ludwig, W. and Teuber, M. (1995). Phylogenetic position of *Gluconobacter* species as a coherent cluster separated from all *Acetobacter* species on the basis of 16S ribosomal RNA sequences, FEMS Microbiol Lett 126, 123-126.
47. Tanasupawat, S., Thawai, C., Yukphan, P., Moonmangmee, D., Itoh, T., Adachi, 0. and Yamada, Y. (2004). *Gluconobacter thailandicus* sp. nov., an acetic acid bacterium in the alpha-Proteobacteria, J Gen Appl Microbiol 50, 159-167.
48. Thompson, F. L., Gevers, D., Thompson, C. C., Dawyndt, P., Naser, S., Hoste, B., Munn, C. B. and Swings, J. (2005). Phylogeny and molecular identification of vibrios on the basis of multilocus sequence analysis, Appl Environ Microbiol 71, 5107-5115.
49. Weyant, R. S., Moss, C. W., Weaver, R. E., Hollis, D. G., Jordan, J. G., Cook, E. C. and Daneshvar, M. I. (1996). Bacterial Identification by Cellular Fatty Analysis. In CDC's Identification of Unusual Pathogenic Gram-Negative and Facultatively Anaerobic Bacteria. Second ed. The Williams & Wilkins Co., Baltimore.
50. Yamada, Y., Katsura, K., Kawasaki, H., Widyastuti, Y., Saono, S., Seki, T., Uchimura, T. and Komagata, K. (2000). *Asaia bogorensis* gen. nov., sp. nov., an unusual acetic acid bacterium in the alpha-Proteobacteria, Int J Syst Evol Microbiol 50 Pt 2, 823-829.
51. Yamashita, S., Uchimura, T., Komagata, K. (2004). Emendation of the genus *Acidimonas* Urakami, Tamaoka, Suzuki and Komagata 1989, Int J syst Evol Microbiol 54, 865-70.
52. Yukphan, P., Malimas, T., Takahashi, M., Potacharoen, W., Busabun, T., Tanasupawat, S., Nakagawa, Y., Tanticharoen, M. and Yamada, Y. (2004a). Re-identification of

*Gluconobacter* strains based on restriction analysis of 16S-23S rDNA internal transcribed spacer regions, J Gen Appl Microbiol 50, 189-195.

53. Yukphan, P., Potacharoen, W., Nakagawa, Y., Tanticharoen, M. and Yamada, Y. (2004b). Identification of 5 strains assigned to the genus *Gluconobacter* Asai 1935 based on the sequence and the restriction analyses of the 16S-23S rDNA internal transcribed spacer regions, J Gen Appl Microbiol 50, 9-15.

54. Zeigler, D. R. (2003). Gene sequences useful for predicting relatedness of whole genomes in bacteria, Int J Syst Evol Microbiol 53, 1893-1900.

TABLE 1

Characteristics that differentiate *Granulibacter* gen. nov. from other genera of acetic acid bacteria

| Characteristic | 1 | 2 | 3 | 4 | 5 | 6 | 7 | 8 | 9 |
|---|---|---|---|---|---|---|---|---|---|
| Flagellation | Non-motile | Peritrichous or non-motile | Peritrichous or non-motile | Polar or non-motile | Non-motile | Non-motile | Peritrichous or non-motile | Non-motile | Non-motile |
| Pigmentation | + | − | − | + | − | − | +/− | − | + |
| Oxidation of: | | | | | | | | | |
| Acetate | W | + | + | − | W | + | W | − | W |
| Lactate | + | + | + | − | W | − | W | − | W |
| Assimilation of ammonium sulfate on glucose medium | W | W | W | − | − | − | + | − | ND |
| Growth on: | | | | | | | | | |
| Glutamate agar | + | + | + | − | − | − | + | + | + |
| Mannitol agar | W | + | W | + | + | − | + | + | + |
| Dihydroxyacetone from glycerol | − | +/− | +/− | + | + | − | +/− | W | + |
| Utilization of methanol | + | − | − | − | − | + | − | − | − |
| Acetic acid from ethanol-CaCO₃ agar: | | | | | | | | | |
| 2-0% CaCO₃ | W/− | + | + | + | + | + | − | + | + |
| 0-6% CaCO₃ | + | ND | + | + | ND | ND | ND | ND | ND |
| 0-1% CaCO₃ | + | ND | + | + | ND | ND | ND | ND | ND |
| Acid production from: | | | | | | | | | |
| Mannitol | − | +/− | − | + | − | − | +/− | W | − |
| Sorbitol | − | − | − | + | − | − | +/− | +(d) | + |
| Dulcitol | − | − | − | − | − | − | + | W | +/− |
| Glycerol | W/− | + | − | + | + | + | + | + | + |
| Ethanol | + | + | + | + | + | + | − | + | + |
| DNA G + C content (mol %) | 59 | 55-56 | 52-60 | 54-63 | 56-57 | 63-66 | 59-61 | 63·1 | 57·6-59·9 |

Genera: 1, *Granulibacter*, 2, *Gluconacetobacter*, 3, *Acetobacter*, 4, *Gluconobacter*, 5, *Kozakia*; 6, *Acidomonas*, 7, *Asaia*; 8, *Neoasaia*, 9, *Swaminathania*. Data for reference taxa were taken from Yamada et al. (2000), Lisdiyanti et al. (2002), Yamashita et al. (2004), Loganathan & Nair (2004) and Yukphan et al. (2005). +, Positive; −, negative; W, weakly positive; d, delayed; ND, not determined.

Table 2

TABLE 2

Calculated percentage similarities for 16S rRNA gene sequences for *Granulibacter bethesdensis* sp. nov. and strains of *Acetobacteraceae*

| Strain | 1 | 2 | 3 | 4 | 5 | 6 | 7 | 8 | 9 |
|---|---|---|---|---|---|---|---|---|---|
| *Acetobacter aceti* NCIMB 8621ᵀ (X74066) | | 96·4 | 94·7 | 91·4 | 91·6 | 91·7 | 87·2 | 94·3 | 95·8 | 95·3 |
| *Asaia bogorensis* NRIC 0311ᵀ (AB025928) | | | 95·8 | 92·1 | 92·5 | 92·2 | 87·8 | 94·7 | 96·5 | 95·4 |
| *Acidomonas methanolica* JCM 6891ᵀ (D30770) | | | | 91·7 | 93·0 | 90·8 | 88·8 | 94·4 | 96·3 | 94·5 |
| *Acidiphilium cryptum* ATCC 33463ᵀ (D30773) | | | | | 93·1 | 93·4 | 88·3 | 92·9 | 92·1 | 90·8 |
| *Acidisphaera rubrifaciens* JCM 10660ᵀ (D86512) | | | | | | 91·2 | 89·9 | 93·5 | 93·8 | 90·9 |
| *Acidocella facilis* ATCC 35904ᵀ (D30774) | | | | | | | 87·0 | 92·6 | 92·4 | 91·8 |
| *Craurococcus roseus* JCM 9933ᵀ (D85828) | | | | | | | | 88·9 | 88·4 | 87·3 |
| *Granulibacter bethesdensis* CGDNIHIᵀ (AY788950) | | | | | | | | | 95·4 | 93·2 |
| *Gluconacetobacter liquefaciens* NBRC 12388ᵀ (X75617) | | | | | | | | | | 93·7 |
| *Gluconobacter oxydans* NCIMB 9013ᵀ (X73820) | | | | | | | | | | |
| *Kozakia baliensis* NRIC 0488ᵀ (AB036321) | | | | | | | | | | |
| *Neoasaia chiangmaiensis* AC28ᵀ (AB208549) | | | | | | | | | | |
| *Paracraurococcus ruber* NS89ᵀ (D85827) | | | | | | | | | | |
| *Rhodopila globiformis* DSM 161ᵀ (D86513) | | | | | | | | | | |
| *Roseomonas gilardii* ATCC 49956ᵀ (AY150045) | | | | | | | | | | |
| *Roseococcus thiosulfatophilus* DSM 8511ᵀ (X72908) | | | | | | | | | | |
| *Saccharibacter floricola* DSM 15669ᵀ (AB110421) | | | | | | | | | | |
| *Stella humosa* DSM 5900ᵀ (AJ535710) | | | | | | | | | | |

| Strain | 10 | 11 | 12 | 13 | 14 | 15 | 16 | 17 | 18 |
|---|---|---|---|---|---|---|---|---|---|
| *Acetobacter aceti* NCIMB 8621ᵀ (X74066) | 96·0 | 95·1 | 88·6 | 92·3 | 89·0 | 88·2 | 93·2 | 86·3 | 96·1 |
| *Asaia bogorensis* NRIC 0311ᵀ (AB025928) | 97·5 | 97·4 | 89·7 | 93·2 | 89·8 | 89·1 | 92·8 | 86·3 | 98·8 |

TABLE 2-continued

Calculated percentage similarities for 16S rRNA gene sequences for *Granulibacter bethesdensis* sp. nov. and strains of Acetobacteraceae

| Strain | Values |
|---|---|
| *Acidomonas methanolica* JCM 6891$^T$ (D30770) | 95.5  95.8  89.6  92.8  90.1  88.7  91.6  86.1  95.2 |
| *Acidiphilium cryptum* ATCC 33463$^T$ (D30773) | 91.6  92.0  90.1  92.7  91.3  88.2  88.1  86.1  91.2 |
| *Acidisphaera rubrifaciens* JCM 10660$^T$ (D86512) | 92.7  92.5  91.2  95.1  91.1  90.1  88.0  85.6  91.8 |
| *Acidocella facilis* ATCC 35904$^T$ (D30774) | 92.4  92.4  89.2  91.8  89.0  88.3  89.8  84.7  92.4 |
| *Craurococcus roseus* JCM 9933$^T$ (D85828) | 88.2  87.9  93.8  90.8  92.9  89.1  85.0  86.0  87.1 |
| *Granulibacter bethesdensis* CGDNIHI$^T$ (AY788950) | 95.0  94.6  89.6  93.7  90.2  88.5  90.4  86.0  94.3 |
| *Gluconacetobacter liquefaciens* NBRC 12388$^T$ (X75617) | 97.2  96.4  89.8  93.8  90.1  89.6  91.9  85.8  96.0 |
| *Gluconobacter oxydans* NCIMB 9013$^T$ (X73820) | 94.8  95.6  88.7  92.1  89.6  87.6  93.8  87.0  95.4 |
| *Kozakia baliensis* NRIC 0488$^T$ (AB036321) | 97.7  89.7  93.8  89.9  88.6  92.3  85.2  97.0 |
| *Neoasaia chiangmaiensis* AC28$^T$ (AB208549) | 85.5  88.6  86.1  84.4  88.3  81.6  92.5 |
| *Paracraurococcus ruber* NS89$^T$ (D85827) | 91.6  93.7  92.2  87.4  86.4  89.4 |
| *Rhodopila globiformis* DSM 161$^T$ (D86513) | 90.9  88.7  87.9  84.9  91.7 |
| *Roseomonas gilardii* ATCC 49956$^T$ (AY150045) | 90.5  86.3  86.8  89.2 |
| *Roseococcus thiosulfatophilus* DSM 8511$^T$ (X72908) | 86.3  84.9  88.8 |
| *Saccharibacter floricola* DSM 15669$^T$ (AB110421) | 86.0  92.9 |
| *Stella humosa* DSM 5900$^T$ (AJ535710) | 85.7 |

Strains: 1, *Asaia bogorensis* NRIC 0311$^T$ (AB025928); 2, *Acidomonas methanolica* JCM 6891$^T$ (D30770); 3, *Acidiphilium cryptum* ATCC 33463$^T$ (D30773); 4, *Acidisphaera rubrifaciens* JCM 10600$^T$ (D86512); 5, *Acidocella facilis* ATCC 35904$^T$ (D30774); 6, *Craurococcus roseus* JCM 9933$^T$ (D85828); 7, *Granulibacter bethesdenis* CGDNIHI$^T$ (AY788950); 8, *Gluconacetobacter liquefaciens* NBRC 12388$^T$ (X75617); 9, *Gluconobacter oxydans* NCIMB 9013$^T$ (X73820); 10, *Kozakia baliensis* NRIC 0488$^T$ (AB056321); 11, *Neonsaia chiangmaiensis* AC28$^T$ (AB208549); 12, *Paracraurococcus ruber* NS89$^T$ (DB5827); 13, *Rhodopila globiformis* DSM 161$^T$ (D86513); 14, *Roseomonas gilardii* ATCC 49956$^T$ (AY150045); 15, *Roseococcus thiosulfatophilus* DSM 8511$^T$ (X72908); 16, *Saccharibacter floricola* DSM 15669$^T$ (AB110421); 17, *Stella humosa* DSM 5900$^T$ (AJ535710); 18, *Swaminathania salitolerans* PAS1$^T$ (AF459454).

Percent identity values for *Granulibacter bethesdensis* bacterium compared with representative members of the Acetobacteraceae ranged from 95.6% with *Gluconacetobacter liquefaciens* to 86.2% with *Stella humosa*.

TABLE 3

| Polypeptide | Most similar polypeptide in the art |
|---|---|
| SEQ ID NO: 3 | 61% similar to the IMP dehydrogenase/GMP reductase: Pyrrolo-quinolone quinone of *Rhodopseudomonas palustris* BisA53 accession ZP_00810772) |
| SEQ ID NO: 4 | 70% similar to the pyrrolo-quinoline quinone of *Bradyrhizobium* sp. BTAi1 accession ZP_00860719.1) |
| SEQ ID NO: 5 | 77% similar to the methanol dehydrogenase MxaF of *Methylobacterium nodulans* accession AAG49450) |
| SEQ ID NO: 6 | 72% similar to the pyrrolo-quinoline quinone of *Bradyrhizobium* sp. BTAi1 accession ZP_00860719) |
| SEQ ID NO: 7 | 64% similar to methanol dehydrogenase subunit 2 precursor of *Paracoccus denitrificans* accession P29898) |
| SEQ ID NO: 13 | 82% similar to the formaldehyde activating enzyme of *Methylosinus* sp. LW2 accession AAS88978) |
| SEQ ID NO: 15 | 54% similar to the methylene tetrahydromethanopterin dehydrogenase of *Hyphomicrobium zavarzinii* accession AAS86340) |
| SEQ ID NO: 17 | 62% similar to the N5N10-methenyltetrahydromethanopterin cyclohydrolase of *Methylocapsa acidiphila* accession CAJ01586) |
| SEQ ID NO: 19 | 62% similar to the formylmethannofuran-tetrahydromethanopterin formyltransferase of *Methylococcus capsulatus* str. Bath accession AAU91105) |
| SEQ ID NO: 21 | 46% similar to the formyltransferase/hydrolase complex Fhc subunit c of *Methylobacterium extorquens* accession AAC26976) |
| SEQ ID NO: 22 | 52% similar to the putative formylmethanofurane dehydrogenase, subunit of *Methylococcus capsulatus* str. Bath accession AAU91628) |
| SEQ ID NO: 23 | 32% similar to the formylmethanofuran dehydrogenase of *Nitrosococcus oceani* ATCC 19707 accession ABA56567) |
| SEQ ID NO: 27 | 62% similar to the mtdA bifunctional protein of *Methylobacterium dichloromethanicum* accession CAD13312) |
| SEQ ID NO: 29 | 64% similar to the methenyl tetrahydrofolate cyclohydrolase of *Magnetospirillum magnetotacticum* MS-1 accession ZP_00052771) |
| SEQ ID NO: 31 | 69% similar to the 10-formyltetrahydrofolate synthetase of *Sphingomonas paucimobilis* accession BAD61061) |
| SEQ ID NO: 33 | 62% similar to the NADH dehydrogenase (ubiquinone), 24 kDa subunit of *Paracoccus denitificans* PD1222 accession ZP_00631273) |
| SEQ ID NO: 34 | 74% similar to the NADH dehydrogenase (quinone) of *Bradyrhizobium* sp. BTAi1 accession ZP_00860091) |
| SEQ ID NO: 35 | 77% similar to the formate dehydrogenase alpha subunit of *Agrobacterium tumefaciens* str. C %* accession AAL45502) |
| SEQ ID NO: 36 | 46% similar to hypothetical protein Magn03005161 of *Magnetospirillum magnetotacticum* MS-1 accession ZP_00051109) |
| SEQ ID NO: 37 | 62% similar to the oxidoreductase alpha (molybdopterin) subunit of *Burkholderia vietnamiensis* G4 accession ZP_00425955) |
| SEQ ID NO: 43 | 51% similar to *Burkholderia cenocepacia* HI2424; accession ZP_00462538 |
| SEQ ID NO: 44 | 54% similar to *Burkholderia dolosa* AUO158; accession ZP_00984559 |
| SEQ ID NO: 45 | 73% similar to *Burkholderia vietnamiensis* G4 accession ZP_00421790 |
| SEQ ID NO: 49 | 59% similar to *Nostoc punctiforme* PCC 73102 accession ZP_00106887 |

TABLE 4

Amino Acid Substitutions

| Original Residue | Exemplary Substitutions |
|---|---|
| Arg | Lys |
| Asn | Gln |
| Asp | Glu |
| Cys | Ser |
| Gln | Asn |

TABLE 4-continued

Amino Acid Substitutions

| Original Residue | Exemplary Substitutions |
| --- | --- |
| Glu | Asp |
| Gly | Pro |
| His | Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09051573B2). An electronic copy of the "Sequence Listing" will also be available from the USPTO upon request and payment of the fee set forth in 37 CFR 1.19(b)(3).

What is claimed is:

1. A biofuel cell, comprising a cathode, an anode, a conductive medium, an ion exchange membrane interposed between the cathode and the anode, and a bacterial catalyst around the anode, wherein the bacterial catalyst comprises an isolated Gram-negative bacterium, wherein the bacterium is an aerobic, facultative methylotroph that produces colonies that are yellow pigmented, wherein the bacterium can use methanol as a sole carbon source and can oxidize glucose and ethanol into acid, and wherein the bacterium comprises a 16SRNA nucleic acid identified as SEQ ID NO:2.

2. The biofuel cell of claim 1, wherein the bacterium is designated Granulibacter bethesdensis and deposited under ATCC Accession No. BAA-1260.

3. The biofuel cell of claim 1, wherein the bacterium can degrade methanol into carbon dioxide and hydrogen ions.

4. The biofuel cell of claim 1, wherein the bacterium can degrade ethanol into acetic acid.

5. The biofuel cell of claim 1, wherein the bacterium comprises a genome identified as SEQ ID NO:1 and is deposited under GenBank Accession No. CP000394.

6. The biofuel cell of claim 1, wherein the bacterium produces methanol dehydrogenase, wherein the methanol dehydrogenase oxidizes methanol into formaldehyde.

7. The biofuel cell of claim 6, wherein the methanol dehydrogenase comprises a first subunit peptide and a second subunit peptide.

8. The biofuel cell of claim 7, wherein the first subunit peptide is a first peptide, a second peptide, a third peptide, or a fourth peptide.

9. The biofuel cell of claim 8, wherein the first peptide of the first subunit has an amino acid sequence identified as SEQ ID NO:3.

10. The biofuel cell of claim 8, wherein the second peptide of the first subunit has an amino acid sequence identified as SEQ ID NO:4.

11. The biofuel cell of claim 8, wherein the third peptide of the first subunit has an amino acid sequence identified as SEQ ID NO:5.

12. The biofuel cell of claim 8, wherein the fourth peptide of the first subunit has an amino acid sequence identified as SEQ ID NO:6.

13. The biofuel cell of claim 8, wherein the second subunit peptide has an amino acid sequence identified as SEQ ID NO:7.

14. The biofuel cell of claim 9, wherein the amino acid sequence identified as SEQ ID NO:3 is encoded by a nucleic acid identified as SEQ ID NO:8.

15. The biofuel cell of claim 10, wherein the amino acid sequence identified as SEQ ID NO:4 is encoded by a nucleic acid identified as SEQ ID NO:9.

16. The biofuel cell of claim 11, wherein the amino acid sequence identified as SEQ ID NO:5 is encoded by a nucleic acid identified as SEQ ID NO:10.

17. The biofuel cell of claim 12, wherein the amino acid sequence identified as SEQ ID NO:6 is encoded by a nucleic acid identified as SEQ ID NO:11.

18. The biofuel cell of claim 13, wherein the amino acid sequence identified as SEQ ID NO:7 is encoded by a nucleic acid identified as SEQ ID NO:12.

19. The biofuel cell of claim 1, wherein the bacterium produces formaldehyde-activating enzyme that has an amino acid sequence identified as SEQ ID NO:13, wherein the formaldehyde-activating enzyme converts formaldehyde into methylene tetrahydromethanopterin.

20. The biofuel cell of claim 19, wherein the amino acid sequence identified as SEQ ID NO:13 is encoded by a nucleic acid identified as SEQ ID NO:14.

21. The biofuel cell of claim 1, wherein the bacterium produces methylenetetrahydromethanopterin dehydrogenase (NAD+/NADP) that has an amino acid sequence identified as SEQ ID NO:15, wherein the methylenetetrahydromethanopterin dehydrogenase (NAD+/NADP) converts methylene tetrahydromethanopterin into methenyl tetrahydromethanopterin.

22. The biofuel cell of claim 21, wherein the amino acid sequence identified as SEQ ID NO:15 is encoded by a nucleic acid identified as SEQ ID NO:16.

23. The biofuel cell of claim 1, wherein the bacterium produces N5N10-methenyltetrahydromethanopterin cyclohydrolase that has an amino acid sequence identified as SEQ ID NO:17, wherein the N5N10-methenyltetrahydromethanopterin cyclohydrolase converts methenyl tetrahydromethanopterin into 5-formyl tetrahydromethanopterin.

24. The biofuel cell of claim 23, wherein the amino acid sequence identified as SEQ ID NO:17 is encoded by a nucleic acid identified as SEQ ID NO:18.

25. The biofuel cell of claim 1, wherein the bacterium produces formylmethanofuran-tetrahydromethanopterin formyltransferase that has an amino acid sequence identified as SEQ ID NO:19, wherein the formylmethanofuran-tetrahydromethanopterin formyltransferase converts 5-formyl tetrahydromethanopterin into formyl methanofuran.

26. The biofuel cell of claim 25, wherein the formylmethanofuran-tetrahydromethanopterin formyltransferase is encoded by a nucleic acid identified as SEQ ID NO:20.

27. The biofuel cell of claim 1, wherein the bacterium produces tungsten-containing formylmethanofuran dehydrogenase that converts formyl methanofuran into formate.

28. The biofuel cell of claim 27, wherein the tungsten-containing formylmethanofuran dehydrogenase comprises a subunit (c) peptide, a subunit (a) peptide, and a subunit (b) peptide.

29. The biofuel cell of claim 28, wherein the subunit (c) peptide has an amino acid sequence identified as SEQ ID NO:21.

30. The biofuel cell of claim 28, wherein the subunit (a) peptide has an amino acid sequence identified as SEQ ID NO:22.

31. The biofuel cell of claim 28, wherein the subunit (b) peptide has an amino acid sequence identified as SEQ ID NO:23.

32. The biofuel cell of claim 29, wherein the amino acid sequence identified as SEQ ID NO:21 is encoded by a nucleic acid identified as SEQ ID NO:24.

33. The biofuel cell of claim 30, wherein the amino acid sequence identified as SEQ ID NO:22 is encoded by a nucleic acid identified as SEQ ID NO:25.

34. The biofuel cell of claim 31, wherein the amino acid sequence identified as SEQ ID NO:23 is encoded by a nucleic acid identified as SEQ ID NO:26.

35. The biofuel cell of claim 1, wherein the bacterium produces methylenetetrahydrofolate dehydrogenase (NADP+) that has an amino acid sequence identified as SEQ ID NO:27, wherein the methylenetetrahydrofolate dehydrogenase (NADP+) converts N5N10-methylene tetrahydrofolate into N5N10-methenyl tetrahydrofolate.

36. The biofuel cell of claim 35, wherein the amino acid sequence identified as SEQ ID NO:27 is encoded by a nucleic acid identified as SEQ ID NO:28.

37. The biofuel cell of claim 1, wherein the bacterium produces methylenetetrahydrofolate cyclohydrolase that has an amino acid sequence identified as SEQ ID NO:29, wherein the methylenetetrahydrofolate cyclohydrolase converts N5N10-methenyl tetrahydrofolate into N10-formyl tetrahydrofolate.

38. The biofuel cell of claim 37, wherein the amino acid sequence identified as SEQ ID NO:29 is encoded by a nucleic acid identified as SEQ ID NO:30.

39. The biofuel cell of claim 1, wherein the bacterium produces formate-tetrahydrofolate ligase that has an amino acid sequence identified as SEQ ID NO:31, wherein the formate-tetrahydrofolate ligase converts N10-formyl tetrahydrofolate into formate.

40. The biofuel cell of claim 39, wherein the amino acid sequence identified as SEQ ID NO:31 is encoded by a nucleic acid identified as SEQ ID NO:32.

41. The biofuel cell of claim 1, wherein the bacterium produces formate dehydrogenase, wherein the formate dehydrogenase converts formate into carbon dioxide.

42. The biofuel cell of claim 41, wherein the formate dehydrogenase comprises a first subunit peptide, a second subunit peptide, a third subunit peptide, a fourth subunit peptide, and a fifth subunit peptide.

43. The biofuel cell of claim 42, wherein the first subunit peptide has an amino acid sequence identified as SEQ ID NO:33.

44. The biofuel cell of claim 42, wherein the second subunit peptide has an amino acid sequence identified as SEQ ID NO:34.

45. The biofuel cell of claim 42, wherein the third subunit peptide has an amino acid sequence identified as SEQ ID NO:35.

46. The biofuel cell claim 42, wherein the fourth subunit peptide has an amino acid sequence identified as SEQ ID NO:36.

47. The biofuel cell of claim 42, wherein the fifth subunit peptide has an amino acid sequence identified as SEQ ID NO:37.

48. The biofuel cell of claim 43, wherein the amino acid sequence identified as SEQ ID NO:33 is encoded by a nucleic acid identified as SEQ ID NO:38.

49. The biofuel cell of claim 44, wherein the amino acid sequence identified as SEQ ID NO:34 is encoded by a nucleic acid identified as SEQ ID NO:39.

50. The biofuel cell of claim 45, wherein the amino acid sequence identified as SEQ ID NO:35 is encoded by a nucleic acid identified as SEQ ID NO:40.

51. The biofuel cell of claim 46, wherein the amino acid sequence identified as SEQ ID NO:36 is encoded by a nucleic acid identified as SEQ ID NO:41.

52. The biofuel cell of claim 47, wherein the amino acid sequence identified as SEQ ID NO:37 is encoded by a nucleic acid identified as SEQ ID NO:42.

53. The biofuel cell of claim 1, wherein the bacterium produces an aldehyde dehydrogenase, wherein the aldehyde dehydrogenase oxidizes acetaldeyde into acetic acid.

54. The biofuel cell of claim 53, wherein the aldehyde dehydrogenase comprises a first subunit peptide, a second subunit peptide, and a third subunit peptide.

55. The biofuel cell of claim 54, wherein the first subunit peptide has an amino acid sequence identified as SEQ ID NO:43.

56. The biofuel cell of claim 54, wherein the second subunit peptide has an amino acid sequence identified as SEQ ID NO:44.

57. The biofuel cell claim 54, wherein the third subunit peptide has an amino acid sequence identified as SEQ ID NO:45.

58. The biofuel cell of claim 55, wherein the amino acid sequence identified as SEQ ID NO:43 is encoded by a nucleic acid identified as SEQ ID NO:46.

59. The biofuel cell of claim 56, wherein the amino acid sequence identified as SEQ ID NO:44 is encoded by a nucleic acid identified as SEQ ID NO:47.

60. The biofuel cell of claim 1, wherein the bacterium produces an alcohol dehydrogenase, wherein the alcohol dehydrogenase oxidizes methanol into formaldehyde or ethanol into acetaldehyde.

61. The biofuel cell of claim 60, wherein the alcohol dehydrogenase has an amino acid sequence identified as SEQ ID NO:48.

62. The biofuel cell of claim 61, wherein the amino acid sequence identified as SEQ ID NO:48 is encoded by a nucleic acid identified as SEQ ID NO:49.

63. A method of degrading an organic material, comprising contacting the organic material with the biofuel cell of claim 1, whereby contacting the organic material with the biofuel cell degrades the organic material.

64. The method of claim 63, wherein the bacterium comprises a genome identified as SEQ ID NO:1 and is deposited under GenBank Accession No. CP000394.

65. The method of claim 63, wherein the organic material comprises methanol.

66. The method of claim 63, wherein the organic material comprises formaldehyde.

67. The method of claim 63, wherein the organic material comprises ethanol.

68. The method of claim 63, wherein the contact occurs at a pH of from about 5.0 to about 7.5.

69. The method of claim 68, wherein the pH is from about 5.5 to about 6.5.

70. A method for growing an isolated Gram-negative bacterium, designated Granulibacter bethesdensis and deposited under ATCC Accession No. BAA-1260, wherein the bacterium is an aerobic, facultative methylotroph that produces colonies that are yellow pigmented, wherein the bacterium can use methanol as a sole carbon source and can oxidize glucose and ethanol into acid, and wherein the bacterium comprises a 16SRNA nucleic acid identified as SEQ ID NO:2, comprising culturing the bacterium at a temperature and in a medium effective to promote growth of the bacterium.

71. The method of claim 70, wherein the temperature is from about 26° C. to about 37° C.

72. The method of claim 71, wherein the temperature is from about 35° C. to about 37° C.

73. The method of claim 70, wherein culturing is at a pH from about 5.0 to about 7.5.

74. The method of claim 73, wherein the pH is from about 5.5 to about 6.5.

75. A method of converting chemical energy in an organic material into electrical energy comprising contacting the organic material with the biofuel cell of claim 1, whereby contacting the organic material with the biofuel cell converts the chemical energy in the organic material into electrical energy.

76. The method of claim 75, wherein the bacterium is designated Granulibacter bethesdensis and deposited under ATCC Accession No. BAA-1260.

* * * * *